(12) United States Patent
Watanabe et al.

(10) Patent No.: US 12,415,769 B2
(45) Date of Patent: *Sep. 16, 2025

(54) VINYLETHER COMPOUNDS AND PROCESSES FOR PREPARING ALDEHYDE COMPOUNDS AND A CARBOXYLATE COMPOUND THEREFROM

(71) Applicant: Shin-Etsu Chemical Co., Ltd., Tokyo (JP)

(72) Inventors: Takeru Watanabe, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 533 days.

This patent is subject to a terminal disclaimer.

(21) Appl. No.: 17/861,622

(22) Filed: Jul. 11, 2022

(65) Prior Publication Data
US 2023/0014797 A1 Jan. 19, 2023

(30) Foreign Application Priority Data

Jul. 13, 2021 (JP) .................................. 2021-115859

(51) Int. Cl.
| | |
|---|---|
| C07C 45/42 | (2006.01) |
| C07C 29/14 | (2006.01) |
| C07C 41/30 | (2006.01) |
| C07C 45/51 | (2006.01) |
| C07C 45/62 | (2006.01) |
| C07C 67/08 | (2006.01) |

(52) U.S. Cl.
CPC .............. *C07C 45/42* (2013.01); *C07C 29/14* (2013.01); *C07C 41/30* (2013.01); *C07C 45/513* (2013.01); *C07C 45/62* (2013.01); *C07C 67/08* (2013.01); *C07B 2200/07* (2013.01); *C07C 2601/08* (2017.05); *C07C 2601/10* (2017.05)

(58) Field of Classification Search
None
See application file for complete search history.

(56) References Cited

U.S. PATENT DOCUMENTS 11,661,390 B2 * 5/2023 Watanabe ............... C07C 41/30
568/352
2017/0342013 A1 11/2017 Wakamori et al.

FOREIGN PATENT DOCUMENTS

JP 2017210469 A 11/2017

OTHER PUBLICATIONS

Conia et al. "On the preparation of cyclopentenones by the action of polyphosphoric acid on esters of -ethylenic acids. Part 1: Practical aspects" Bulletin de la Societe Chimique de France, No. 8-9, pp. 2981-2991 (1970) (English machine translation).
Hajare et al. "Enantiospecific synthesis of sex pheromone of the obscure mealybug from pantolactone via tandem conjugate addition/cyclization" Tetrahedron Letters, 51:5291-5293 (2010).
Millar et al. "(2,3,4,4-Tetramethylcyclopentyl)methyl acetate, a sex pheromone from the obscure mealybug: first example of a new structural class of monoterpenes" Journal of Chemical Ecology, 31(12):2999-3005 (2005).
Millar et al. "Stereoselective synthesis of the obscure mealybug pheromone by hydrogenation of a tetrasubstituted alkene precursor" Tetrahedron Letters, 52:4224-4226 (2011).
Millar et al. "Synthesis of the sex pheromone of the obscure mealybug, the first example of a new class of monoterpenoids" Tetrahedron Letters, 48:6377-6379 (2007).
Morel-Fourrier et al. "Acylation of Alkenes Generated in Situ by Hydride Transfer from Isoalkanes. Synthesis of Pentalenones, Hydrindenones, and Cyclopentenones" Journal of the American Chemical Society, 113(21):8062-8069 (1991).
Extended European Search Report corresponding to European Patent Application No. 22183978.0 (6 pages) (dated Nov. 30, 2022).
Thomas et al. "Synthesis and stereochemistry of hydrogenated 1,1,4,4,7a-pentamethylindenes" Canadian Journal of Chemistry, 58(17):1810-1820 (1980).
Zou et al. "Stereoselective synthesis of the obscure mealybug pheromone by hydrogenation of a tetrasubstituted alkene precursor" Tetrahedron Letters, 52:4224-4226 (2011).

* cited by examiner

*Primary Examiner* — Amy C Bonaparte
(74) *Attorney, Agent, or Firm* — Myers Bigel, P.A.

(57) ABSTRACT

The present invention provides a vinylether compound of the following general formula (1), wherein $R^1$ represents a monovalent hydrocarbon group having 1 to 15 carbon atoms, and the wavy line represents the E-form, the Z-form, or a mixture thereof. The present invention further provides a process for preparing 2,3,4,4-tetramethyl-1-cyclopentenecarbaldehyde of the following formula of the following formula (2), the process comprising subjecting the vinylether compound (1) to a hydrolysis reaction to form 2,3,4,4-tetramethyl-1-cyclopentenecarbaldehyde (2).

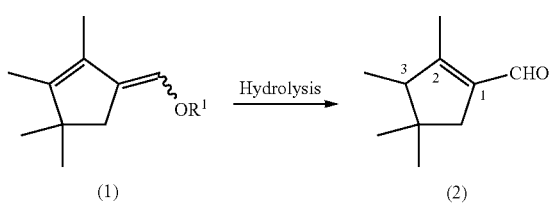

11 Claims, No Drawings

VINYLETHER COMPOUNDS AND PROCESSES FOR PREPARING ALDEHYDE COMPOUNDS AND A CARBOXYLATE COMPOUND THEREFROM

TECHNICAL FIELD

The present invention relates to a vinylether compound. The present invention relates also to processes for preparing an aldehyde compound, i.e., 2,3,4,4-tetramethyl-1-cyclopentenecarbaldehyde and 2,3,4,4-tetramethylcyclopentanecarbaldehyde, and a carboxylate compound, i.e., a (2,3,4,4-tetramethylcyclopentyl)methyl carboxylate compound from the vinylether compounds.

BACKGROUND ART

Insect sex pheromones are biologically active substances which are usually borne by females to attract males, and exhibit a high attracting activity in a small amount. Sex pheromones are widely utilized as a means for forecasting outbreaks of pests and/or confirming their geographic spread (invasion into a specific area), and also as a means for controlling pests. Widely used methods for controlling pests include a mass trapping method, a lure-and-kill or attract-and-kill method, a lure-and-infect or attract-and-infect method, and a mating disruption method. A naturally occurring sex pheromone can be extracted only in a trace amount from one insect. Therefore, it is difficult to use a naturally occurring sex pheromone for a mating disruption method. Before practical use of a sex pheromone, it is required to artificially produce a sufficient amount of a sex pheromone for basic research and also for applications.

*Pseudococcus viburni* (generic name: Obsucure Mealybug, hereinafter abbreviated as "OMB"), which has spread mainly in the American continent, damages various crops including grapes and, therefore, is an economically serious insect. Recently, OMB has been increasingly spreading, and monitoring its geographic spread is important. The sex pheromone of OMB is reported to be (2,3,4,4-tetramethylcyclopentyl)methyl acetate which is one of (2,3,4,4-tetramethylcyclopentyl)methyl carboxylate compounds (Non-Patent Literature 1 listed below). It is also reported that in an attraction test for males with a synthetic racemic mixture of (1R*,2R*,3S*)-(2,3,4,4-tetramethylcyclopentyl)methyl acetate, the synthetic product exhibits an attracting activity comparable to that of the naturally occurring pheromone (Non-Patent Literature 1).

The sex pheromone of OMB is synthesized, for example, by subjecting a starting material, isobutyl methacrylate to a Nazarov cyclization reaction (Non-Patent Literature 1 listed below). Improvements over the method described in Non-Patent Literature 1 are reported (Non-Patent Literatures 2 and 3 listed below). Specifically, methylenation of a ketone with dibromomethane, zinc, and titanium(IV) chloride is carried out to improve a yield. Another process for synthesizing the optically active substance is also reported, in which (−)-pantolactone is used as a starting material, and a tandem conjugate addition/cyclization reaction is carried out as a key step (Non-Patent Literature 4 listed below). Also, a process intended to industrially produce the sex pheromone is disclosed by Wakamori et al., in which a Favorskii rearrangement reaction of α-halotetramethyl cyclohexanone is utilized (Patent Literature 1 listed below).

LIST OF THE LITERATURES

Patent Literature

[Patent Literature 1] Japanese Patent Application Laid-Open No. 2017-210469

Non-Patent Literatures

[Non-Patent Literature 1] J. Millar et al., J. Chem. Ecol., 31, 2999 (2005)
[Non-Patent Literature 2] J. Millar et al., Tetrahedron Lett., 48, 6377 (2007)
[Non-Patent Literature 3] J. Millar et al., Tetrahedron Lett., 52, 4224 (2011)
[Non-Patent Literature 4] D. Reddy et al., Tetrahedron Lett., 51, 5291 (2010)
[Non-Patent Literature 5] Bull. Soc. Chem. Fr., 2981 (1970)
[Non-Patent Literature 6] J. Am. Chem. Soc., 113, 8062 (1991)

Problems to be Solved by the Invention

The preparation process described in Non-Patent Literature 1 comprises less steps, but uses preparative gas chromatography to purify the target compound (2,3,4,4-tetramethylcyclopentyl)methyl acetate, and, therefore, the preparation of a large amount of (2,3,4,4-tetramethylcyclopentyl)methyl acetate in this preparation process is difficult. The preparation processes described in Non-Patent Literatures 2 and 3 require mutagenic dibromomethane and an oxidation reaction with highly toxic hexavalent chromium, as well as silica gel column chromatography which is costly and is difficult to scale up, for the purification of intermediates. This makes the preparation processes difficult to carry out in an industrial scale. The preparation process described in Non-Patent Literature 4 requires so many steps as 17 to synthesize the target compound (2,3,4,4-tetramethylcyclopentyl)methyl acetate from (−)-pantolactone, comprises a conjugate addition reaction at an ultralow temperature of −78° C., and uses an explosive high-valent iodine reagent in an oxidation reaction. This makes the preparation process difficult to carry out in an industrial scale.

On the other hand, although the process described in Patent Literature 1 is more industrially practical, there is demand for a more regioselective preparation process than the Favorskii rearrangement reaction.

Thus, it is difficult to industrially prepare a sufficient amount of (2,3,4,4-tetramethylcyclopentyl)methyl acetate in the known preparation processes, because of the use of the harmful reactants, the number of steps, the means for separation or purification of intermediates and/or the target compound, and other reasons. The known preparation processes also have room for improvement in the reaction selectivity.

SUMMARY OF THE INVENTION

The present invention has been made in these circumstances and aims to provide a process for preparing a (2,3,4,4-tetramethylcyclopentyl)methyl carboxylate compound without any harmful reactant in less steps and with industrially feasible means for purification.

The present invention also aims to provide a process for preparing a racemic mixture of (2,3,4,4-tetramethylcyclopentyl)methyl acetate, which has the same 2-dimensional structure as the sex pheromone of OMB, in a sufficient amount for biological studies, agricultural studies, and/or practical uses, in consideration of the attracting activity of the racemic mixture. More preferably, the present invention aims to provide a process for stereoselectively preparing (1R*,2R*,3S*)-(2,3,4,4-tetramethylcyclopentyl)methyl acetate having the relative configuration same as that of the naturally occurring sex pheromone of OMB, among four diastereomers of (2,3,4,4-tetramethylcyclopentyl)methyl acetate, in a diastereomeric ratio, dr, of 50% or more. The diastereomeric ratio, dr, refers to the number of moles of one diastereomer of interest divided by the total number of moles of all diastereomers present and multiplied by 100, expressed in %.

As a result of the intensive researches, the present inventors have found that a certain vinylether compound and an aldehyde compound, i.e., 2,3,4,4-tetramethyl-1-cyclopentenecarbaldehyde are useful intermediates for the preparation of a carboxylate compound, i.e., a (2,3,4,4-tetramethylcyclopentyl)methyl carboxylate compound.

As a result of the intensive researches, the present inventors have also found that the (2,3,4,4-tetramethylcyclopentyl)methyl carboxylate compound may be industrially prepared via the two intermediates in less steps without any harmful reactants.

As a result of the intensive researches, the present inventors have further found that a racemic mixture of (2,3,4,4-tetramethylcyclopentyl)methyl acetate may be prepared and that among the four diastereomers of (2,3,4,4-tetramethylcyclopentyl)methyl acetate, (1R*,2R*,3S*)-(2,3,4,4-tetramethylcyclopentyl)methyl acetate having the relative configuration same as that of the naturally occurring sex pheromone of OMB may be prepared in a diastereomeric ratio, dr, of 50% or more.

One aspect of the present invention provides a process for preparing 2,3,4,4-tetramethyl-1-cyclopentenecarbaldehyde of the following formula (2), the process comprising:
  subjecting a vinylether compound of the following general formula (1) to a hydrolysis reaction to form 2,3,4,4-tetramethyl-1-cyclopentenecarbaldehyde (2):

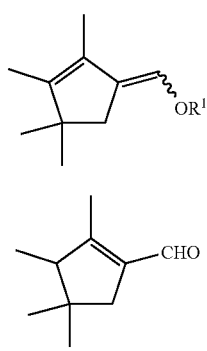

wherein in the general formula (1), $R^1$ represents a monovalent hydrocarbon group having 1 to 15 carbon atoms, and the wavy line represents the E-form, the Z-form, or a mixture thereof.

Another aspect of the present invention provides a process for preparing 2,3,4,4-tetramethylcyclopentanecarbaldehyde of the following formula (3), the process comprising:
  the aforesaid process for preparing 2,3,4,4-tetramethyl-1-cyclopentenecarbaldehyde (2), and
  subjecting 2,3,4,4-tetramethyl-1-cyclopentenecarbaldehyde (2) thus obtained to a hydrogenation reaction to form 2,3,4,4-tetramethylcyclopentanecarbaldehyde (3):

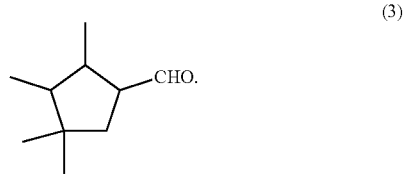

Another aspect of the present invention also provides a process for preparing a (2,3,4,4-tetramethylcyclopentyl)methyl carboxylate compound of the following general formula (5), the process comprising:
  the aforesaid process for preparing 2,3,4,4-tetramethylcyclopentanecarbaldehyde (3),
  subjecting 2,3,4,4-tetramethylcyclopentanecarbaldehyde (3) thus obtained to a reduction reaction with a reducing agent to form (2,3,4,4-tetramethylcyclopentyl)methanol of the following formula (4), and subjecting (2,3,4,4-tetramethylcyclopentyl)methanol (4) thus obtained to an esterification reaction to form the (2,3,4,4-tetramethylcyclopentyl)methyl carboxylate compound (5):

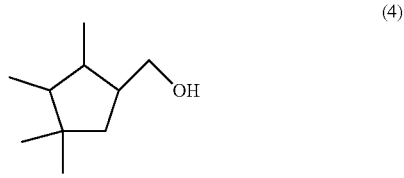

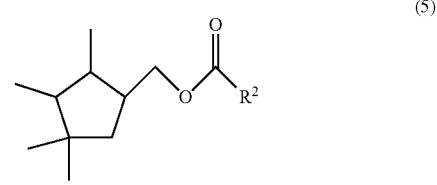

wherein in the general formula (5), $R^2$ represents a hydrogen atom or a monovalent hydrocarbon group having 1 to 15 carbon atoms.

Another aspect of the present invention also provides the process described immediately above for preparing the (2,3,4,4-tetramethylcyclopentyl)methyl carboxylate is (2,3,4,4-compound (5), wherein the carboxylate compound (5) is (2,3,4,4-tetramethylcyclopentyl)methyl acetate of the following formula (5A) and comprises (1R*,2R*,3S*)-(2,3,4,4-tetramethylcyclopentyl)methyl acetate of the following formula (5A') in a diastereomeric ratio, dr, of 50% or more among four diastereomers of (2,3,4,4-tetramethylcyclopentyl)methyl acetate:

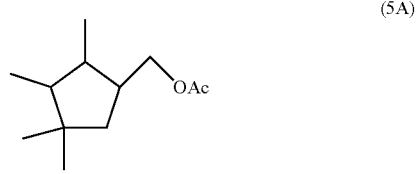

(5A')

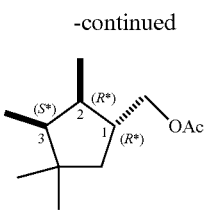

wherein in the formulae (5A) and (5A'), Ac represents an acetyl group, and (R*), (S*), the bold bond, and the hashed bond represents a relative configuration (hereafter the same).

Another aspect of the present invention further provides the aforesaid process for preparing 2,3,4,4-tetramethyl-1-cyclopentenecarbaldehyde (2), 2,3,4,4-tetramethylcyclopentanecarbaldehyde (3), or the (2,3,4,4-tetramethylcyclopentyl)methyl carboxylate compound (5), the process further comprising subjecting 2,3,4,4-tetramethyl-2-cyclopentenone of the following formula (6) to a Wittig reaction with a phosphorus ylide compound of the following general formula (7) to form the vinylether compound (1):

(6)

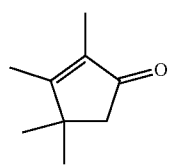

(7)

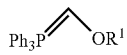

wherein in the general formula (7), R¹ represents a monovalent hydrocarbon group having 1 to 15 carbon atoms, and Ph represents a phenyl group.

Another aspect of the present invention also provides a vinylether compound of the following general formula (1):

(1)

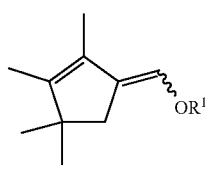

wherein R¹ represents a monovalent hydrocarbon group having 1 to 15 carbon atoms, and the wavy line represents the E-form, the Z-form, or a mixture thereof.

Another aspect of the present invention further provides 2,3,4,4-tetramethyl-1-cyclopentenecarbaldehyde of the following formula (2):

(2)

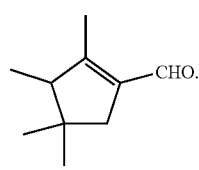

The present invention makes it possible to prepare safely, efficiently, selectively, and industrially a (2,3,4,4-tetramethylcyclopentyl)methyl carboxylate compound, particularly (1R*,2R*,3S*)-(2,3,4,4-tetramethylcyclopentyl)methyl acetate which is promising as a sex pheromone of a serious agricultural pest, OMB, in applications such as forecasting outbreaks of the pest and controlling the pest. The present invention also makes it possible to prepare the vinylether compound (1) and 2,3,4,4-tetramethyl-1-cyclopentenecarbaldehyde (2) which are useful intermediates for the preparation of a (2,3,4,4-tetramethylcyclopentyl)methyl carboxylate compound.

DETAILED DESCRIPTION OF THE PREFERRED EMBODIMENTS

Embodiments of the present invention will be explained below in detail. It should be understood that the present invention is not limited to or by the following embodiments. The intermediates, the reagents, and the target compounds represented by the chemical formulae may comprise stereoisomers such as enantiomers and diastereoisomers. Unless otherwise stated, the chemical formulae shall be interpreted to represent all of these isomers. The isomer may be either alone or in combination thereof.

The present inventors have contemplated, as described below, a plan for the synthesis of the (2,3,4,4-tetramethylcyclopentyl)methyl carboxylate compound (5), which is a target compound of the present invention.

Retrosynthetic analysis is represented, for example, by the following reaction formula for (1R*,2R*,3S*)-(2,3,4,4-tetramethylcyclopentyl)methyl acetate (5A'), which is a racemic mixture of the sex pheromone of OMB, among the (2,3,4,4-tetramethylcyclopentyl)methyl carboxylate compounds (5).

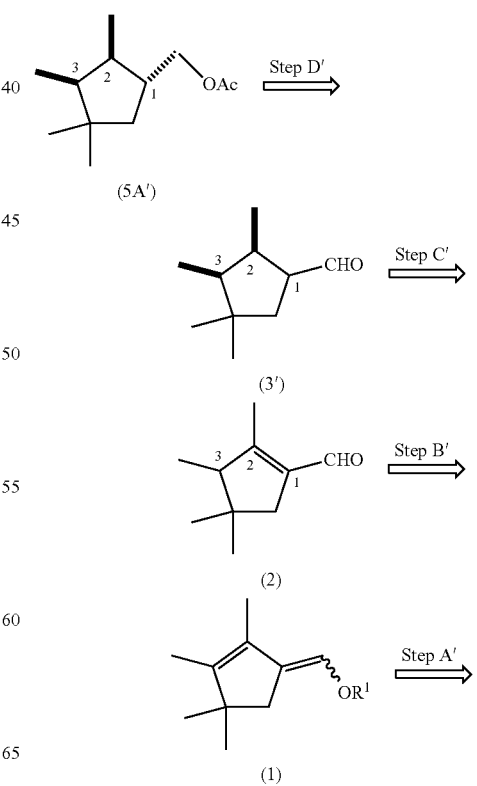

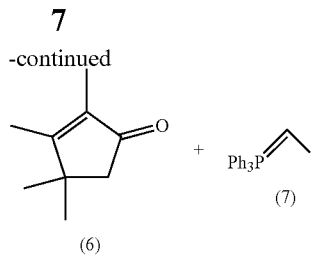

(6)          (7)

wherein R¹ represents a monovalent hydrocarbon group having 1 to 15 carbon atoms, the wavy line represents the E-form, the Z-form, or a mixture thereof, and the bold bond and the hashed bond represents a relative configuration.

In reaction formulae of the retrosynthetic analysis shown above, the open arrows represent transforms in the retrosynthetic analysis.

Step D'

It is thought that (1R*,2R*,3S*)-(2,3,4,4-tetramethylcyclopentyl)methyl acetate (5A') is possible to be synthesized from (1RS,2R*,3S*)-2,3,4,4-tetramethylcyclopentanecarbaldehyde of the formula (3') among 2,3,4,4-tetramethylcyclopentanecarbaldehyde (3). Specifically, the synthesis may be achieved by carrying out two or three steps of 1) if necessary, stereoisomerization (epimerization) at position 1 of (1RS,2R*,3S*)-2,3,4,4-tetramethylcyclopentanecarbaldehyde (3'); 2) reduction of the aldehyde to an alcohol; and 3) esterification of the alcohol.

Step C'

It is thought that (1RS,2R*,3S*)-2,3,4,4-Tetramethylcyclopentanecarbaldehyde (3') is possible to be synthesized by subjecting 2,3,4,4-tetramethyl-1-cyclopentenecarbaldehyde of the formula (2) to a reduction reaction, preferably a hydrogenation reaction of the double bond. A hydrogen atom is expected to add at position 2 from the less sterically hindered side of 2,3,4,4-tetramethyl-1-cyclopentenecarbaldehyde (2), i.e., the opposite side of the methyl group at position 3 to preferentially generate a cis-form having the desired configuration of the two methyl groups at positions 2 and 3. When (1RS,2R*,3S*)-2,3,4,4-tetramethylcyclopentanecarbaldehyde (3') having the 2,3-cis configuration is once obtained, stereoisomerization is unlikely to occur in subsequent conversions, so that the desired 2,3-cis configuration is kept in the target compound. Therefore, it is extremely important to select 2,3,4,4-tetramethyl-1-cyclopentenecarbaldehyde (2) as a substrate and carry out a hydrogenation reaction of the double bond which is expected to undergo stereoselective hydrogenation. Hydrogenation reactions may be carried out generally using very inexpensive molecular hydrogen and a small amount of a reusable hydrogenation catalyst, which is advantageous in view of the industrial economy.

Step B'

It is thought that 2,3,4,4-Tetramethyl-1-cyclopentenecarbaldehyde (2) is possible to be synthesized by subjecting a vinylether compound of the general formula (1) to a hydrolysis reaction. It is thought that when the hydrolysis reaction of the vinylether compound (1) forms an aldehyde, the endocyclic double bond shifts from a position between position 2 and position 3 of the starting material to a thermodynamically more stable position between position 1 and position 2 on account of conjugation with the carbonyl group of the aldehyde. Thus, isomerization occurs easily.

Step A'

It is thought that the vinylether compound (1) is possible to be synthesized by subjecting 2,3,4,4-tetramethyl-2-cyclopentenone of the formula (6), which is a known ketone, to a Wittig reaction with a phosphorus ylide compound of the formula (7).

In consideration of the retrosynthetic analysis mentioned above, an embodiment of the present invention may be depicted by the following chemical reaction scheme.

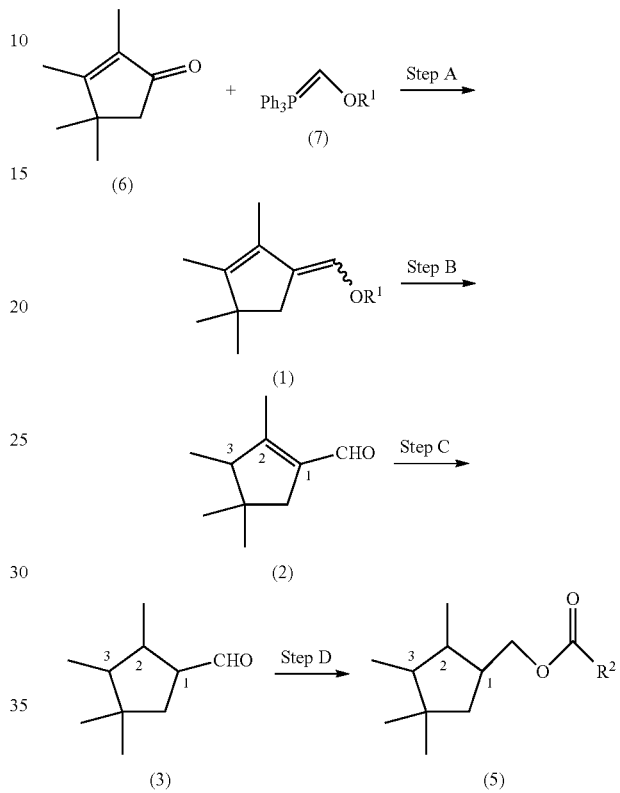

(Step A) 2,3,4,4-Tetramethyl-2-cyclopentenone (6) is subjected to a Wittig reaction with a phosphorus ylide compound (7) to form a vinylether compound (1), as shown in the chemical reaction formula above.

(Step B) Next, the vinylether compound (1) obtained according to step A is subjected to a hydrolysis reaction to form 2,3,4,4-tetramethyl-1-cyclopentenecarbaldehyde (2).

(Step C) 2,3,4,4-Tetramethyl-1-cyclopentenecarbaldehyde (2) obtained according to step B is subjected to a hydrogenation reaction to form 2,3,4,4-tetramethylcyclopentanecarbaldehyde (3).

(Step D) 2,3,4,4-Tetramethylcyclopentanecarbaldehyde (3) is subjected to 1) if necessary, stereoisomerization (epimerization) at position 1 of 2,3,4,4-tetramethylcyclopentanecarbaldehyde (3), 2) reduction of the aldehyde into an alcohol, and 3) esterification of the alcohol to form a (2,3,4,4-tetramethylcyclopentyl)methyl carboxylate compound (5) which is the target compound.

As an exemplary embodiment of the present invention, steps A to D based on the retrosynthetic analysis will be explained in detail below in the order of step B, step A, step C, and step D.

[1] Step B

Step B to prepare 2,3,4,4-tetramethyl-1-cyclopentenecarbaldehyde (2) of the following general formula (2) will be explained below. 2,3,4,4-Tetramethyl-1-cyclopentenecarbaldehyde (2) is prepared by subjecting a vinylether compound of the following general formula (1) to hydrolysis, as shown in the following chemical reaction formula:

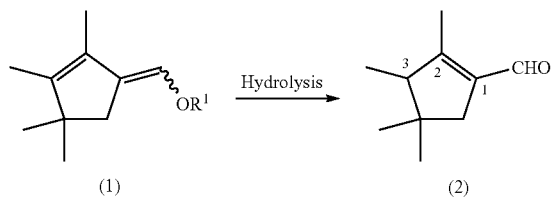

In the general formula, $R^1$ is as defined above, and the wavy line represents the E-form, the Z-form, or a mixture thereof.

First, the vinylether compound of the following general formula (1), which is the starting material of step B, will be explained.

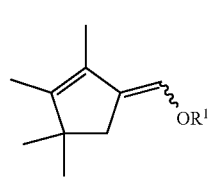

In the general formula (1), $R^1$ represents a monovalent hydrocarbon group having 1 to 15, preferably 1 to 7, more preferably 1 to 4 carbon atoms, and the wavy line represents the E-form, the Z-form, or a mixture thereof.

Examples of the monovalent hydrocarbon group include linear saturated hydrocarbon groups such as a methyl group, an ethyl group, a propyl group, a butyl group, a pentyl group, a hexyl group, a decyl group, an undecyl group, and a pentadecyl group; branched saturated hydrocarbon groups such as an isopropyl group, an s-butyl group, a t-butyl group, and an isobutyl group; cyclic saturated hydrocarbon groups such as a cyclohexyl group; unsaturated hydrocarbon groups such as an allyl group; aryl groups such as a phenyl group; and aralkyl groups such as a benzyl group and a phenethyl group. A methyl group, an ethyl group, a phenyl group, and a benzyl group are particularly preferred in view of the economy. A part of the hydrogen atoms in the hydrocarbon group may be substituted and is preferably substituted with a halogen group, an alkoxy group having 1 to 4 carbon atoms, an alkylthio group, and a trialkylsilyl group. Substituted hydrocarbon groups are more specifically a 2-(trimethylsilyl)ethyl group, a 2-methoxyethyl group, a 2-(methylthio)ethyl group, a chlorophenyl group, or a methoxyphenyl group.

Specific examples of the vinylether compound (1) include 4-(methoxymethylene)-1,1,2,3-tetramethyl-2-cyclopentene, 4-(ethoxymethylene)-1,1,2,3-tetramethyl-2-cyclopentene, 4-(propoxymethylene)-1,1,2,3-tetramethyl-2-cyclopentene, 4-(butoxymethylene)-1,1,2,3-tetramethyl-2-cyclopentene, 4-(pentadecyloxymethylene)-1,1,2,3-tetramethyl-2-cyclopentene, 4-(isopropoxymethylene)-1,1,2,3-tetramethyl-2-cyclopentene, 4-(cyclohexyloxymethylene)-1,1,2,3-tetramethyl-2-cyclopentene, 4-(allyloxymethylene)-1,1,2,3-tetramethyl-2-cyclopentene, 4-(phenoxymethylene)-1,1,2,3-tetramethyl-2-cyclopentene, 4-(benzyloxymethylene)-1,1,2,3-tetramethyl-2-cyclopentene, 4-[2-(trimethylsilyl)ethoxymethylene]-1,1,2,3-tetramethyl-2-cyclopentene, 4-[(2-methoxyethoxy)methylene]-1,1,2,3-tetramethyl-2-cyclopentene, 4-[2-(methylthio)ethoxymethylene]-1,1,2,3-tetramethyl-2-cyclopentene, 4-[(4-chlorophenoxy)methylene]-1,1,2,3-tetramethyl-2-cyclopentene, and 4-[(4-methoxyphenoxy)methylene]-1,1,2,3-tetramethyl-2-cyclopentene. 4-(Methoxymethylene)-1,1,2,3-tetramethyl-2-cyclopentene, 4-(ethoxymethylene)-1,1,2,3-tetramethyl-2-cyclopentene, 4-(phenoxymethylene)-1,1,2,3-tetramethyl-2-cyclopentene, and 4-(benzyloxymethylene)-1,1,2,3-tetramethyl-2-cyclopentene are preferred in view of the availability of raw materials and/or the costs of production.

A process for preparing the vinylether compound (1) will be explained in step A described below.

Next, 2,3,4,4-tetramethyl-1-cyclopentenecarbaldehyde (2), which is the target compound of step B, is represented by the following formula (2):

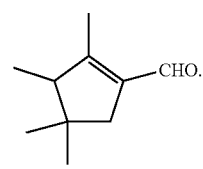

The hydrolysis reaction may be carried out by adding water and an acid and/or a solvent, if necessary, to the vinylether compound (1). The hydrogenation reaction may be carried out with cooling or heating.

An amount of the water used in the hydrolysis reaction may be arbitrarily set as long as a practically sufficient reaction rate is achieved. The amount is preferably from 0.1 to 100,000 mol, more preferably from 0.5 to 10,000 mol, even more preferably from 1 to 1,000 mol, per mol of the vinylether compound (1).

The acid used in the hydrolysis reaction is preferably commercially available in large amounts. Examples of the acid include inorganic acids such as hydrochloric acid, hydrobromic acid, hydroiodic acid, sulfuric acid, nitric acid, and phosphoric acid, or salts thereof; organic acids such as formic acid, acetic acid, propionic acid, oxalic acid, trifluoroacetic acid, methanesulfonic acid, benzenesulfonic acid, p-toluenesulfonic acid, trifluoromethanesulfonic acid, and naphthalenesulfonic acid, or salts thereof; Lewis acids such as lithium tetrafluoroborate, boron trifluoride, boron trichloride, boron tribromide, aluminum trichloride, zinc chloride, zinc bromide, zinc iodide, tin tetrachloride, tin tetrabromide, tin dichloride, titanium tetrachloride, titanium tetrabromide, and trimethylsilyl iodide; oxides such as alumina, silica gel, and titania; various cation exchange resins; and minerals such as montmorillonite. Hydrochloric acid, sulfuric acid, nitric acid, phosphoric acid, formic acid, acetic acid, oxalic acid, and p-toluenesulfonic acid are preferred in view of the economy and/or reactivity.

The acid may be used alone or in combination thereof, if necessary. The acid may be commercially available one.

An amount of the acid may be arbitrarily set as long as a practically sufficient reaction rate is achieved. The amount is preferably as small as possible in view of the economy and is preferably from 0.00001 to 10,000 mol, more preferably from 0.0001 to 1,000 mol, even more preferably from 0.001 to 100 mol, per mol of the vinylether compound (1).

A solvent other than water may be incorporated in the hydrolysis reaction.

Examples of the solvent include ethers such as diethyl ether, dibutyl ether, tetrahydrofuran, and 1,4-dioxane; hydrocarbons such as hexane, heptane, benzene, toluene, xylene, and cumene; chlorinated solvents such as methylene chloride, chloroform, and trichloroethylene; ketones such as acetone and methyl ethyl ketone; aprotic polar solvents such as N,N-dimethylformamide (DMF), 1,3-dimethyl-2-imidazolidinone (DMI), dimethyl sulfoxide (DMSO), and hexamethylphosphoric triamide (HMPA); nitriles such as acetonitrile and propionitrile; esters such as ethyl acetate and n-butyl acetate; and alcohols such as methanol, ethanol, and t-butyl alcohol. The solvent is preferably an ether such as diethyl ether or tetrahydrofuran or a mixed solvent containing an ether.

The solvent may be used alone or in combination thereof, if necessary. The solvent may be commercially available one.

An amount of the solvent is preferably from 10 g to 10,000 g, per mol of the vinylether compound (1).

A reaction temperature in the hydrolysis reaction depends on reaction conditions and is preferably from −78 to 160° C., more preferably from −50 to 140° C., even more preferably from −30 to 120° C.

A reaction time of the hydrolysis reaction may be arbitrarily set. In view of the yield, it is desirable to monitor progress of the reaction with gas chromatography (GC) and/or silica gel thin layer chromatography (TLC) to complete the reaction. The reaction time is typically and preferably from 0.5 to 100 hours.

It is thought that when the hydrolysis reaction of the vinylether compound (1) forms an aldehyde, the double bond originally at position 2 shifts to thermodynamically more stable position 1 on account of conjugation with the carbonyl group of the aldehyde and easily causes isomerization so as to mainly form 2,3,4,4-tetramethyl-1-cyclopentenecarbaldehyde (2).

In the hydrolysis reaction, an alcohol $R^1OH$, which is a reaction side product, may react with the vinylether compound (1), which is the starting material, or 2,3,4,4-tetramethyl-1-cyclopentenecarbaldehyde (2), which is the desired product, to form an undesired acetal compound as a byproduct. To prevent the by-production of the undesired acetal compound, the hydrolysis reaction may be done while removing the resulting alcohol $R^1OH$ out of the reaction system by distillation or other methods.

When 2,3,4,4-tetramethyl-1-cyclopentenecarbaldehyde (2) obtained in the hydrolysis reaction has a sufficient purity for a subsequent step, a crude product or a reaction mixture filtrate may be used as such in the subsequent step. Alternatively, when it is desired to separate and remove impurities such as possibly intermixed regioisomers on the double bond, they may be removed in any purification method used in ordinary organic syntheses, such as distillation and/or various chromatography. The purification is preferably distillation, for example distillation under reduced pressure, in view of the industrial economy.

[2] Step A

Step A to prepare a vinylether compound of the following general formula (1) will be explained below. The vinylether compound (1) is prepared by subjecting 2,3,4,4-tetramethyl-2-cyclopentenone of the following formula (6) to a Wittig reaction with a phosphorus ylide compound (7) of the following formula (7), as shown in the following chemical reaction formula:

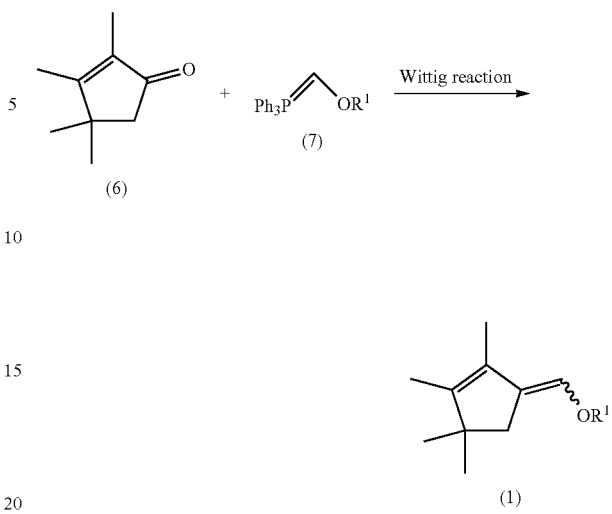

wherein $R^1$ represents a monovalent hydrocarbon group having 1 to 15 carbon atoms, Ph represents a phenyl group, and the wavy line represents the E-form, the Z-form, or a mixture thereof.

2,3,4,4-Tetramethyl-2-cyclopentenone (6), which is the starting material of step A, is a known compound and may be easily prepared in one step, for example, according to a method described in Bull. Soc. Chim. Fr., 2981 (1970) or J. Am. Chem. Soc., 113, 8062 (1991).

Next, the phosphorus ylide compound (7) will be explained below.

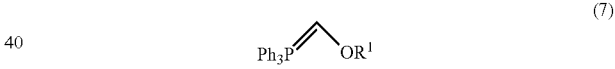

$R^1$ in the general formula (7) is as defined for the general formula (1).

Specific examples of the phosphorus ylide compound (7) include (methoxymethylene)triphenylphosphorane, (ethoxymethylene)triphenylphosphorane, (propoxymethylene)triphenylphosphorane, (butoxymethylene)triphenylphosphorane, (decyloxymethylene)triphenylphosphorane, (pentadecyloxymethylene)triphenylphosphorane, (isopropoxymethylene)triphenylphosphorane, (cyclohexyloxymethylene)triphenylphosphorane, (allyloxymethylene) triphenylphosphorane, (phenoxymethylene)triphenylphosphorane, (benzyloxymethylene)triphenylphosphorane, triphenyl[2-(trimethylsilyl)ethoxymethylene]phosphorane, [(2-methoxyethoxy)methylene]triphenylphosphorane, [2-(methylthio)ethoxymethylene]triphenylphosphorane, [(4-chlorophenoxy)methylene]triphenylphosphorane, and [(4-methoxyphenoxy)methylene]triphenylphosphorane.

(Methoxymethylene)triphenylphosphorane, (ethoxymethylene)triphenylphosphorane, (phenoxymethylene)triphenylphosphorane, and (benzyloxymethylene)triphenylphosphorane are preferred in view of the availability of raw materials and/or the production cost.

A process for preparing the phosphorus ylide compound (7) is not particularly limited, and the phosphorus ylide compound (7) is prepared, for example, by subjecting a triphenylphosphonium halide compound (101) to a dehydrohalogenation reaction in the presence of a base, as shown in the following reaction formula.

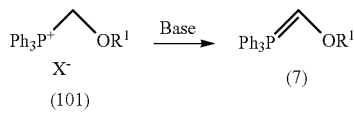

R¹ in the general formula is as defined for the general formula (1). X represents a halogen atom, preferably a chlorine atom, a bromine atom, or an iodine atom. Ph represents a phenyl group.

R¹ in the general formula (101) is as defined for the general formula (1). X represents a halogen atom, preferably a chlorine atom, a bromine atom, or an iodine atom. Specific examples of the triphenylphosphonium halide compound (101) include (methoxymethyl)triphenylphosphonium chloride, (methoxymethyl)triphenylphosphonium bromide, (methoxymethyl triphenylphosphonium)iodide, (ethoxymethyl)triphenylphosphonium chloride, (butoxymethyl)triphenylphosphonium chloride, (pentadecyloxymethyl)triphenylphosphonium chloride, (isopropoxymethyl) triphenylphosphonium chloride, (cyclohexyloxymethyl) triphenylphosphonium chloride, (allyloxymethyl) triphenylphosphonium chloride, (phenoxymethyl) triphenylphosphonium chloride, (benzyloxymethyl) triphenylphosphonium chloride, triphenyl[2-(trimethylsilyl) ethoxymethylene]phosphonium chloride, [(2-methoxyethoxy)methyl)triphenylphosphonium chloride, [2-(methylthio) ethoxymethyl)triphenylphosphonium chloride, [(4-chlorophenoxy)methyl)triphenylphosphonium chloride, and [(4-methoxyphenoxy)methyl)triphenylphosphonium chloride.

The triphenylphosphonium halide compound (101) may be commercially available one or may be prepared by a reaction between a halide of the following general formula (102) and triphenylphosphine, i.e., PPh₃, to form the quaternary phosphonium salt

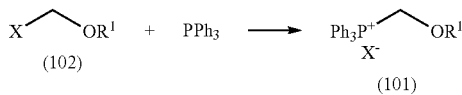

In the general formulae, R¹, X, and Ph are as defined above.

Specific examples of the halide (102) include chloromethyl methyl ether, bromomethyl methyl ether, iodomethyl methyl ether, chloromethyl ethyl ether, butyl chloromethyl ether, chloromethyl pentadecyl ether, chloromethyl isopropyl ether, cyclohexyl chloromethyl ether, allyl chloromethyl ether, chloromethyl phenyl ether, benzyl chloromethyl ether, 2-methoxyethoxymethyl chloride, chloromethyl 2-(trimethylsilyl)ethyl ether, chloromethyl 2-(methylthio) ethoxymethyl ether, chloromethyl 4-chlorophenyl ether, and chloromethyl 4-methoxyphenyl ether.

In the preparation of the triphenylphosphonium halide compound (101), a metal halide and/or a quaternary onium salt may be incorporated to accelerate the reaction.

Example of the metal halide include lithium iodide, sodium iodide, potassium iodide, lithium bromide, sodium bromide, and potassium bromide.

Example of the quaternary onium salt include tetraethylammonium bromide, tetrabutylammonium bromide, tetrabutylphosphonium bromide, tetraethylammonium iodide, tetrabutylammonium iodide, and tetrabutylphosphonium iodide.

In the preparation of the triphenylphosphonium halide compound (101), the reaction may be carried out in a basic condition by adding bicarbonates such as lithium bicarbonate, sodium bicarbonate, and potassium bicarbonate; carbonates such as lithium carbonate, sodium carbonate, and potassium carbonate; hydroxide salts such as lithium hydroxide, sodium hydroxide, and potassium hydroxide; or organic bases such as triethylamine, diisopropylethylamine, tributylamine, N,N-dimethylaniline, N,N-diethylaniline, pyridine, 4-dimethylaminopyridine, quinoline, pyrrolidine, piperidine, collidine, lutidine, and morpholine.

The triphenylphosphonium halide compound (101) is preferably prepared in a solvent.

Example of the solvent include ethers such as diethyl ether, dibutyl ether, tetrahydrofuran, and 1,4-dioxane; hydrocarbons such as hexane, heptane, benzene, toluene, xylene, and cumene; chlorinated solvents such as methylene chloride, chloroform, and trichloroethylene; aprotic polar solvents such as N,N-dimethylformamide, N,N-dimethylacetamide, N-methylpyrrolidone, 1,3-dimethyl-2-imidazolidinone, dimethyl sulfoxide, and hexamethylphosphoric triamide; nitriles such as acetonitrile and propionitrile; esters such as ethyl acetate and n-butyl acetate; and alcohols such as methanol, ethanol, and t-butyl alcohol. The solvent may be used alone or in combination thereof.

An amount of the solvent is preferably from 10 g to 10,000 g, per mol of the halide (102).

A reaction temperature in the preparation of the triphenylphosphonium halide compound (101) may be appropriately selected, depending on starting materials. Typically, the reaction temperature is from −10° C. to 180° C., preferably from 0° C. to 160° C., more preferably from 10° C. to 140° C.

A reaction time of the preparation of the triphenylphosphonium halide compound (101) may be arbitrarily set. In view of the yield, it is desirable to monitor progress of the reaction with gas chromatography (GC) and/or silica gel thin layer chromatography (TLC) to complete the reaction. The reaction time is typically and preferably from 0.5 to 60 hours.

Examples of the base used in the preparation of the phosphorus ylide compound (7) include metal alkoxides such as sodium methoxide, sodium ethoxide, sodium t-butoxide, sodium t-amiloxide, lithium methoxide, lithium ethoxide, lithium t-butoxide, lithium t-amiloxide, potassium methoxide, potassium ethoxide, potassium t-butoxide, and potassium t-amiloxide; organometallic reagents such as methyllithium, ethyllithium, n-butyllithium, methylmagnesium chloride, sodium acetylide, and dimsyl sodium; metal amides such as sodium amide, lithium amide, lithium diisopropylamide, lithium hexamethyldisilazide, sodium hexamethyldisilazide, potassium hexamethyldisilazide, and lithium dicyclohexylamide; and metal hydrides such as sodium hydride, potassium hydride, and calcium hydride.

The base may be used alone or in combination thereof, if necessary, and is chosen, depending on the triphenylphosphonium halide compound (101) which is a substrate, and/or reactivity and/or reaction yield. The base may be commercially available one.

An amount of the base used in the preparation of the phosphorus ylide compound (7) is preferably from 0.7 mol to 5 mol, per mol of the triphenylphosphonium halide compound (101).

The solvent used in the preparation of the phosphorus ylide compound (7) may be same as that used in the preparation of the triphenylphosphonium halide compound (101).

A reaction temperature in the preparation of the phosphorus ylide compound (7) is preferably from −78 to 50° C., more preferably from −78° C. to 35° C.

A reaction time of the preparation of the phosphorus ylide compound (7) is preferably from 5 minutes to 18 hours, more preferably from 5 minutes to 10 hours, in view of the stability of the reactants.

Next, the vinylether compound (1), which is the target compound of step A, is as explained in [1] above.

The Wittig reaction may be carried out by adding 2,3,4,4-tetramethyl-2-cyclopentenone (6) to a solvent. The Wittig reaction may be carried out with cooling or heating.

An amount of 2,3,4,4-tetramethyl-2-cyclopentenone (6) used in the Wittig reaction is from 0.1 mol to 5 mol, preferably from 0.2 mol to 3 mol, per theoretical mol of the phosphorus ylide compound (7).

The solvent used in the Wittig reaction may be same as that used in the preparation of the triphenylphosphonium halide compound (101).

An amount of the solvent used in the Wittig reaction is preferably from 10 g to 10,000 g, per theoretical mol of the phosphorus ylide compound (7).

A reaction temperature of the Wittig reaction is preferably from −78° C. to 50° C., more preferably from −50° C. to 35° C.

A reaction time of the Wittig reaction may be arbitrarily set. In view of the yield, it is desirable to monitor progress of the reaction with gas chromatography (GC) and/or silica gel thin layer chromatography (TLC) to complete the reaction. The reaction time is typically and preferably from 0.5 to 24 hours.

When the vinylether compound (1) obtained in the Wittig reaction has a sufficient purity for a subsequent step, a crude product or a reaction mixture or a reaction mixture filtrate may be used as such in the subsequent step. Alternatively, when it is desired to separate and remove impurities, they may be removed in any purification method used in ordinary organic syntheses, such as distillation and/or various chromatography. The purification is preferably distillation, for example distillation under reduced pressure, in view of the industrial economy.

The vinylether compound (1) obtained in the Wittig reaction has two geometric isomers, the E-form and Z-form, on account of the geometrical isomerism of the exocyclic double bond. Thus, the vinylether compound (1) is usually present as a mixture of the two isomers, and the mixture may be used as such in a subsequent step without the need to separate the geometric isomers.

[3] Step C

Step C to prepare 2,3,4,4-tetramethylcyclopentanecarbaldehyde of the following formula (3) will be explained below. 2,3,4,4-Tetramethylcyclopentanecarbaldehyde (3) is prepared by subjecting 2,3,4,4-tetramethyl-1-cyclopentenecarbaldehyde (2) obtained in step B to a hydrogenation reaction, as shown in the following chemical reaction formula.

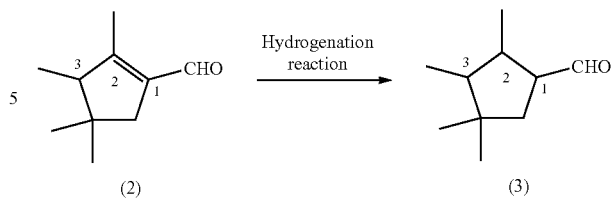

2,3,4,4-Tetramethyl-1-cyclopentenecarbaldehyde (2), which is the starting material of step C, is as explained in [1] above.

Next, 2,3,4,4-tetramethylcyclopentanecarbaldehyde (3), which is the target compound of step C, will be explained below.

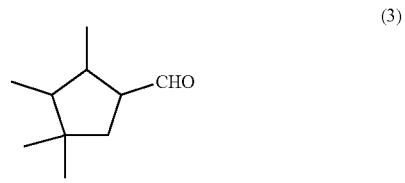

2,3,4,4-Tetramethylcyclopentanecarbaldehyde (3) has four diastereomers as follows: (1R*,2R*,3R*)-2,3,4,4-tetramethylcyclopentanecarbaldehyde (hereinafter referred to also as (1R*,2R*,3R*)-form), (1R*,2S*,3R*)-2,3,4,4-tetramethylcyclopentanecarbaldehyde (hereinafter referred to also as (1R*,2S*,3R*)-form), (1R*,2S*,3S*)-2,3,4,4-tetramethylcyclopentanecarbaldehyde (hereinafter referred to also as (1R*,2S*,3S*)-form), and (1R*,2R*,3S*)-2,3,4,4-tetramethylcyclopentanecarbaldehyde of the following formula (3″) (hereinafter referred to also as (1R*,2R*,3S*)-form (3″)). The (1R*,2R*,3S*)-form (3″) has the relative configuration same as that of the sex pheromone of OMB.

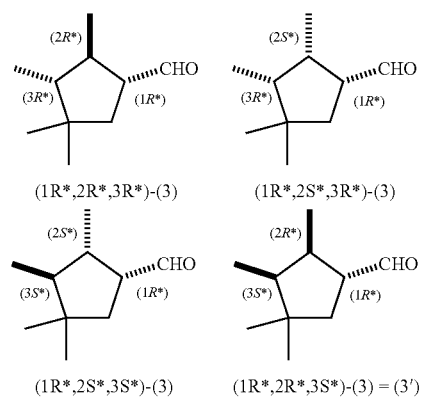

In the formulae (3), the bold bond and the hashed bond represents a relative configuration.

The hydrogenation reaction may be carried out by reacting 2,3,4,4-tetramethyl-1-cyclopentenecarbaldehyde (2) with hydrogen in the presence of a hydrogenation catalyst in a solvent, if necessary. The hydrogenation reaction may be carried out with cooling or heating.

Examples of the hydrogenation catalyst include metals (referred to also as metal catalysts) such as cobalt, nickel, rhodium, palladium, ruthenium, osmium, platinum, iridium, copper, and iron and metal oxides (referred to also as metal oxide catalysts) of these metals; metal hydroxides such as palladium hydroxide and rhodium hydroxide; metal halides such as palladium chloride, ruthenium chloride, and rhodium chloride; and complex compounds such as chloroplatinic acid and chlorotris(triphenylphosphine) rhodium.

The hydrogenation catalyst may be a metal catalyst or a metal oxide catalyst, as mentioned above, supported on a carrier. Examples of the carrier include carbon, alumina, zeolite, and silica gel. The carrier is preferably carbon. Specific examples of the hydrogenation catalyst supported on carbon include rhodium on carbon, palladium on carbon, ruthenium on carbon, platinum on carbon, and palladium hydroxide on carbon. Rhodium on carbon, palladium on carbon, and palladium hydroxide on carbon are particularly preferred.

The hydrogenation catalyst may be used alone or in combination thereof, if necessary. The hydrogenation catalyst may be commercially available one.

An amount of the hydrogenation catalyst may be arbitrarily set as long as a practically sufficient reaction rate is achieved. The amount is preferably as small as possible in view of the economy and is preferably from 0.00001 to 10 mol, more preferably from 0.00001 to 1 mol, even more preferably from 0.00001 to 0.5 mol, per mol of 2,3,4,4-tetramethyl-1-cyclopentenecarbaldehyde (2).

Examples of the solvent used in the hydrogenation reaction include alcohols such as methanol, ethanol, isopropyl alcohol, t-butyl alcohol, benzyl alcohol, methoxyethanol, ethoxyethanol, diethyleneglycol monomethyl ether, and triethyleneglycol monomethyl ether; ethers such as diethyl ether, di-n-butyl ether, tetrahydrofuran, and 1,4-dioxane; hydrocarbons such as hexane, heptane, benzene, toluene, xylene, and cumene; aprotic polar solvents such as N,N-dimethylformamide (DMF), 1,3-dimethyl-2-imidazolidinone (DMI), dimethyl sulfoxide (DMSO), and hexamethylphosphoric triamide (HMPA); nitriles such as acetonitrile and propionitrile; carboxylic acids such as formic acid, acetic acid, and trifluoroacetic acid; and water.

The solvent may be used alone or in combination thereof, if necessary. The solvent may be commercially available one.

An amount of the solvent is preferably from 0.01 parts by mass to 100,000 parts by mass, more preferably from 0.1 parts by mass to 10,000 parts by mass, per 100 parts by mass of 2,3,4,4-tetramethyl-1-cyclopentenecarbaldehyde (2).

A hydrogen pressure used in the hydrogenation reaction is preferably from normal pressure to 5 MPa.

A reaction temperature of the hydrogenation reaction may be arbitrarily set as long as a practically sufficient reaction rate is achieved. The reaction temperature is preferably from −20° C. to 150° C., more preferably from 0° C. to 100° C.

A reaction time of the hydrogenation reaction may be arbitrarily set. In view of the yield, it is desirable to monitor progress of the reaction with gas chromatography (GC) and/or thin layer chromatography (TLC) to complete the reaction. The reaction time is typically and preferably from 5 minutes to 240 hours.

When 2,3,4,4-tetramethylcyclopentanecarbaldehyde (3) obtained in the hydrogenation reaction has a sufficient purity for a subsequent step, a crude product or a reaction mixture or a reaction mixture filtrate may be used as such in the subsequent step. Alternatively, when it is desired to separate and remove impurities, they may be removed in any purification method used in ordinary organic syntheses, such as distillation and/or various chromatography. The purification is preferably distillation, for example distillation under reduced pressure, in view of the industrial economy.

For the preparation of (1R*,2R*,3S*)-(2,3,4,4-tetramethylcyclopentyl)methyl acetate (5A') which is a racemic mixture of the sex pheromone of OMB, (1RS,2R*,3S*)-2,3,4,4-tetramethylcyclopentanecarbaldehyde of the following formula (3') (hereinafter referred to also as (1RS,2R*,3S*)-form (3')) which has two methyl groups at positions 2 and 3 of 2,3,4,4-tetramethylcyclopentanecarbaldehyde (3) of the following formula in cis configuration is more preferable than (1RS,2S*,3S*)-2,3,4,4-tetramethylcyclopentanecarbaldehyde (3) (hereinafter referred to also as (1RS,2S*,3S*)-form) which has two methyl groups at positions 2 and 3 in trans configuration.

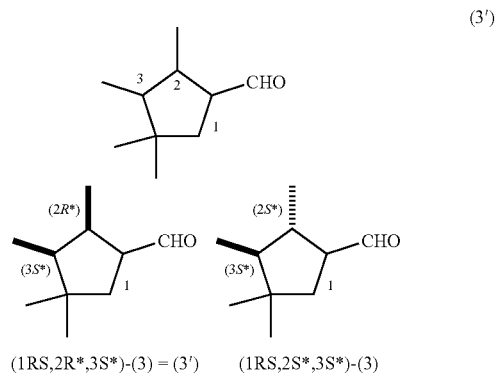

(1RS,2R*,3S*)-(3) = (3')     (1RS,2S*,3S*)-(3)

To preferentially prepare the (1RS,2R*,3S*)-form (3'), the hydrogenation catalyst is preferably a metal such as rhodium or palladium, a metal oxide of these metals, or a metal catalyst or metal oxide catalyst supported on a carrier such as carbon, alumina, zeolite, or silica gel. The carrier is particularly preferably carbon. Specifically, rhodium on carbon, palladium on carbon, and palladium hydroxide on carbon are more particularly preferred. Generally, a hydrogen atom tends to add from a less sterically hindered side of a substrate molecule in the hydrogenation reaction with such a hydrogenation catalyst. Therefore, it is thought that a hydrogen atom preferentially adds from the less sterically hindered side of 2,3,4,4-tetramethyl-1-cyclopentenecarbaldehyde (2), i.e., the opposite side of the methyl group at position 3 to selectively give the desired 2,3-cis configuration, as shown in the following chemical reaction formula. The relative configuration of the two methyl groups at positions 2 and 3 of the (1RS,2R*,3S*)-form (3') obtained in step C is kept in subsequent steps in the final compound is obtained. Therefore, it is very important to increase stereoselectivity in step C for increasing the diastereomeric ratio of the target compound.

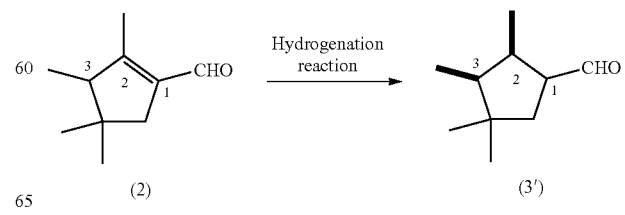

[4] Step D

Step D to prepare a (2,3,4,4-tetramethylcyclopentyl) methyl carboxylate compound of the following general formula (5) will be explained below. The (2,3,4,4-tetramethylcyclopentyl)methyl carboxylate compound (5) is prepared by subjecting 2,3,4,4-tetramethylcyclopentanecarbaldehyde (3) obtained in step C to a reduction reaction with a reducing agent to form (2,3,4,4-tetramethylcyclopentyl) methanol of the following formula (4) and then subjecting (2,3,4,4-tetramethylcyclopentyl)methanol (4) thus prepared to an esterification reaction, as shown in the following chemical reaction formula.

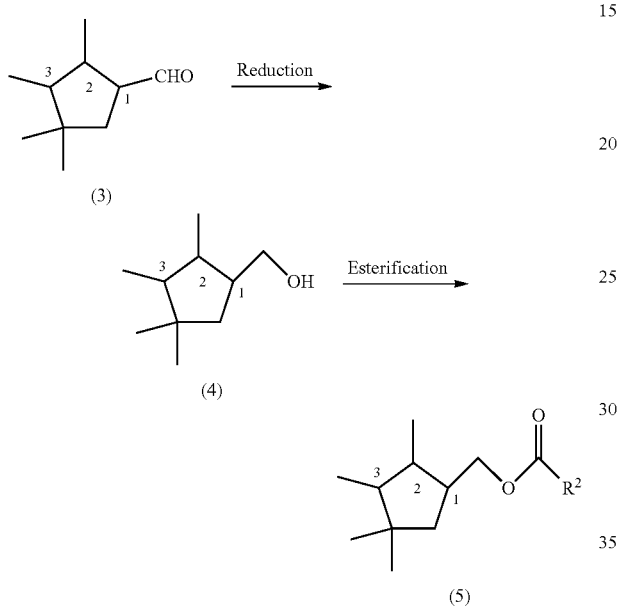

2,3,4,4-Tetramethylcyclopentane carbaldehyde (3), which is the starting material of step D, is as explained in [3] above.

(2,3,4,4-Tetramethylcyclopentyl)methanol, which is an intermediate of step D, is represented by the following formula (4).

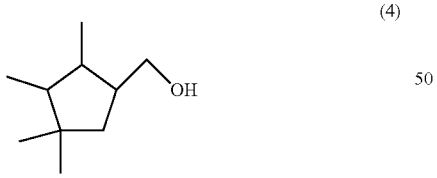

(2,3,4,4-Tetramethylcyclopentyl)methanol (4) has four diastereomers as follows: (1R*,2R*,3R*)-(2,3,4,4-tetramethylcyclopentyl)methanol (hereinafter referred to also as (1R*,2R*,3R*)-form), (1R*,2S*,3R*)-(2,3,4,4-tetramethylcyclopentyl)methanol (hereinafter referred to also as (1R*, 2S*,3R*)-form), (1R*,2S*,3S*)-(2,3,4,4-tetramethylcyclopentyl)methanol (hereinafter referred to also as (1R*,2S*, 3S*)-form), and (1R*,2R*,3S*)-(2,3,4,4-tetramethylcyclopentyl)methanol (4') of the following formula (4') (hereinafter referred to also as (1R*,2R*,3S*)-form (4')). The (1R*,2R*,3S*)-form (4') has the relative configuration same as that of the sex pheromone of OMB.

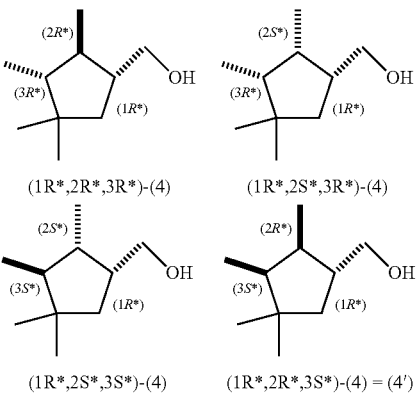

In the formulae (4), the bold bond and the hashed bond represents a relative configuration.

(2,3,4,4-Tetramethylcyclopentyl)methanol (4) is preferably (1R*,2R*,3S*)-(2,3,4,4-tetramethylcyclopentyl) methanol of the following formula (4') in view of the preparation of (1R*,2R*,3S*)-(2,3,4,4-tetramethylcyclopentyl)methyl acetate (5A') which is a racemic mixture of the sex pheromone of OMB, that is, to prepare (1R*,2R*, 3S*)-(2,3,4,4-tetramethylcyclopentyl)methyl acetate in a diastereomeric ratio, dr, of 50% or more.

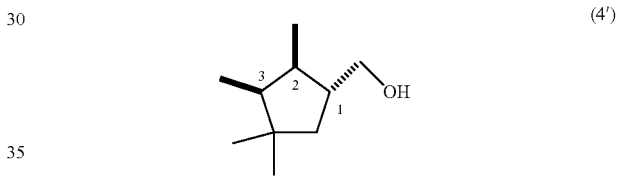

The (2,3,4,4-tetramethylcyclopentyl)methyl carboxylate compound (5), which is the target compound of step D, is represented by the following general formula (5):

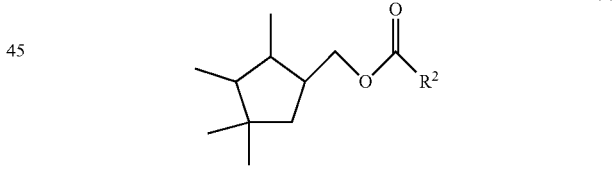

wherein $R^2$ represents a hydrogen atom or a monovalent hydrocarbon group having 1 to 15 carbon atoms.

Specific examples of the 2,3,4,4-tetramethylcyclopentyl) methyl carboxylate compound (5) include (2,3,4,4-tetramethylcyclopentyl)methyl formate, (2,3,4,4-tetramethylcyclopentyl)methyl acetate, (2,3,4,4-tetramethylcyclopentyl) methyl propionate, (2,3,4,4-tetramethylcyclopentyl)methyl butyrate, (2,3,4,4-tetramethylcyclopentyl)methyl pentanoate, (2,3,4,4-tetramethylcyclopentyl)methyl isobutyrate, (2,3,4,4-tetramethylcyclopentyl)methyl isovalerate, (2,3,4, 4-tetramethylcyclopentyl)methyl 3-methyl-3-butenoate, (2,3,4,4-tetramethylcyclopentyl)methyl tiglate, (2,3,4,4-tetramethylcyclopentyl)methyl senecioate, (2,3,4,4-tetramethylcyclopentyl)methyl acrylate, (2,3,4,4-tetramethylcyclopentyl)methyl methacrylate, and (2,3,4,4-tetramethylcyclopentyl)methyl 2-acetoxy-3-methyl butanoate.

Among (2,3,4,4-tetramethylcyclopentyl)methyl carboxylate compounds (5), (2,3,4,4-tetramethylcyclopentyl)methyl acetate, which has a methyl group $R^2$ in the general formula (5) and is represented by the following general formula (5A), has the same 2-dimensional structural formula as that of the sex pheromone of a serious pest, OMB, and is industrially valuable.

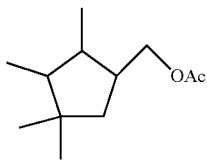

(5A)

wherein Ac represents an acetyl group.

(2,3,4,4-Tetramethylcyclopentyl)methyl acetate (5A) represented by the 2-dimensional structural formula of the sex pheromone of OMB has four diastereomers that are specifically as follows: (1R*,2R*,3R*)-2,3,4,4-tetramethylcyclopentyl)methyl acetate (hereinafter referred to also as (1R*,2R*,3R*)-form); (1R*,2S*,3R*)-2,3,4,4-tetramethylcyclopentyl)methyl acetate (hereinafter referred to also as (1R*,2S*,3R*)-form); (1R*,2S*,3S*)-2,3,4,4-tetramethylcyclopentyl)methyl acetate (hereinafter also as (1R*,2S*,3S*)-form); and referred to (1R*,2R*,3S*)-(2,3,4,4-tetramethylcyclopentyl)methyl acetate of the following formula (5A') (hereinafter referred to also as (1R*,2R*,3S*)-form (5A')). The (1R*,2R*,3S*)-form (5A') has the relative configuration same as that of the sex pheromone of OMB.

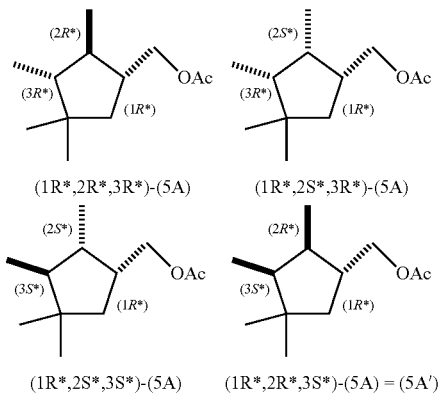

In the formulae (5A), Ac represents an acetyl group. (R*), (S*), the bold bond, and the hashed bond represents a relative configuration.

Among (2,3,4,4-tetramethylcyclopentyl)methyl acetate compounds (5A), the (1R*,2R*,3S*)-form (5A') having a relative configuration of (1R*,2R*,3S*), which is a racemic mixture of the sex pheromone of OMB, has been already confirmed to have an attracting activity for males of OMB as mentioned above and is industrially valuable.

The racemic mixture of the sex pheromone of OMB means a 1:1 mixture of the following (1S,2S,3R)-(2,3,4,4-tetramethylcyclopentyl)methyl acetate (1S,2S,3R)-(5A'), which is the sex pheromone of OMB, and its enantiomer (1R,2R,3S)-(2,3,4,4-tetramethylcyclopentyl)methyl acetate (1R,2R,3S)-(5A').

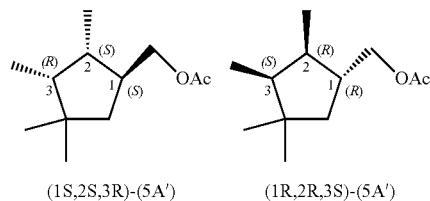

In the formulae, (R), (S), a bold wedged bond, and a hashed wedge bond represent the absolute configuration.

In the non-stereoselective preparation, the (1R*,2R*,3S*)-form (5A') having the relative configuration same as that of the naturally occurring sex pheromone of OMB is prepared in an expected diastereomeric ratio of only around 25% dr. In a non-stereoselective preparation actually carried out in Non-Patent Literature 1, the (1R*,2R*,3S*)-form (5A') was prepared in a diastereomeric ratio of less than 20% dr. The three diastereomers other than the (1R*,2R*,3S*)-form (5A') that account for 80% or more of all diastereomers have no activity for OMB, and there are concerns that contamination with large amounts of such inactive components may have some adverse effects on practical uses. For example, if the diastereomeric ratio decreases by half in the production of an amount of the active component, the total production amount is required to be doubled to obtain the amount of the active component. Therefore, a higher diastereomeric ratio is advantageous in view of the industrial economy.

The 2,3,4,4-tetramethylcyclopentyl)methyl carboxylate compound (5) is preferable to be (2,3,4,4-tetramethylcyclopentyl)methyl acetate (5A) in view of the advantage in the application for controlling OMB. Moreover, the (1R*,2R*,3S*)-form (5A') has preferably a diastereomeric ratio, dr, of 50% or more, more preferably 60% or more, even more preferably 70% or more.

In the reduction step, (2,3,4,4-tetramethylcyclopentyl)methanol (4) is prepared by subjecting the substrate 2,3,4,4-tetramethylcyclopentanecarbaldehyde (3) to a reduction reaction with a reducing agent, as shown in the following chemical reaction formula.

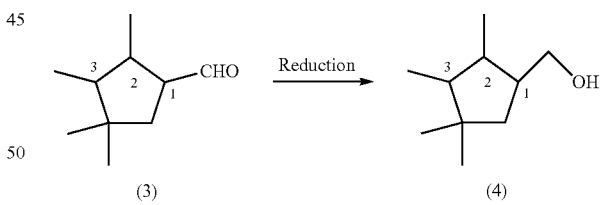

The reduction reaction may be a known reduction reaction of an aldehyde into an alcohol. In the reduction reaction, the substrate is typically reacted with a reducing agent in a solvent with cooling or heating, if necessary.

Examples of the reducing agent used in the reduction reaction include hydrogen; boron compounds such as a borane, an alkylborane, a dialkylborane, and a bis(3-methyl-2-butyl) borane; metal hydrides s a dialkylsilane, a trialkylsilane, a monoalkylaluminum hydride, and a dialkylaluminum hydride; complex hydrides such as sodium borohydride, lithium borohydride, potassium borohydride, calcium borohydride, sodium aluminum hydride, lithium aluminum hydride, sodium trimethoxyborohydride, lithium trimethoxyaluminum hydride, lithium diethoxyaluminum hydride, lithium tri(tert-butoxy)aluminum hydride, sodium bis(2-methoxyethoxy)aluminum hydride, and lithium triethylborohydride; and an alkoxy or alkyl derivative thereof. Hydrogen or complex hydrides are preferred in view of reaction conditions and/or easy work-up and/or easy product isolation.

When hydrogen is used as a reducing agent in the reduction reaction, the reduction reaction may be carried out in a similar manner to the hydrogenation reaction in step C described above.

The reduction reaction with a reducing agent other than hydrogen will be explained in detail below.

An amount of the reducing agent used in the reduction reaction varies, depending on a species of a reducing agent and/or reaction conditions to be used, and is typically and preferably from 0.1 mol to a large excessive amount (2 mol to 500 mol), more preferably from 0.2 mol to 8.0 mol, per mol of the substrate 2,3,4,4-tetramethylcyclopentanecarbaldehyde (3).

Examples of the solvent used in the reduction reaction include water; hydrocarbons such as hexane, heptane, benzene, toluene, xylene, and cumene; ethers such as diethyl ether, di-n-butyl ether, diethyleneglycol diethyl ether, diethyleneglycol dimethyl ether, tetrahydrofuran, and 1,4-dioxane; alcohols such as methanol, ethanol, 1-propanol, 2-propanol, ethyleneglycol monomethyl ether, and diethyleneglycol monomethyl ether; nitriles such as acetonitrile; ketones such as acetone and 2-butanone; esters such as ethyl acetate and n-butyl acetate; and aprotic polar solvents such as N,N-dimethylformamide, dimethyl sulfoxide, and hexamethylphosphoric triamide.

The solvent may be used alone or in combination thereof, if necessary. The solvent may be commercially available one.

The solvent used in the reduction reaction is appropriately selected, depending on a species of a reducing agent to be used. Examples of a preferred combination of the reducing agent and the solvent include a combination of lithium borohydride as the reducing agent with an ether, a mixed solvent of an ether and an alcohol, or a mixed solvent of an ether and a hydrocarbon; a combination of lithium aluminum hydride as the reducing agent with an ether or a mixed solvent of an ether and a hydrocarbon; and a combination of sodium borohydride as the reducing agent with an alcohol, a mixed solvent of an ether and water, a mixed solvent of a hydrocarbon and water, or a mixed solvent of an ether and an alcohol.

An amount of the solvent used in the reduction reaction is preferably from 0.01 parts by mass to 100,000 parts by mass, more preferably from 0.1 parts by mass to 10,000 parts by mass, per 100 parts by mass of the substrate 2,3,4,4-tetramethylcyclopentanecarbaldehyde (3).

A reaction temperature in the reduction reaction varies, depending on a species of a reagent and/or solvent to be used. For example, when lithium aluminum hydride is used as a reducing agent in tetrahydrofuran, the reaction temperature is preferably from −78° C. to 50° C., more preferably from −70° C. to 20° C.

A reaction time of the reduction reaction may be arbitrarily set. In view of the yield, it is desirable to monitor progress of the reaction with gas chromatography (GC) and/or silica gel thin layer chromatography (TLC) to complete the reaction. The reaction time is typically and preferably from 0.5 to 100 hours.

Next, in the esterification step, a (2,3,4,4-tetramethylcyclopentyl)methyl carboxylate compound (5) is prepared by subjecting (2,3,4,4-tetramethylcyclopentyl)methanol (4) to an esterification reaction, as shown in the following chemical reaction formula. Hereinafter, (2,3,4,4-tetramethylcyclopentyl)methanol (4) which is a reaction substrate is referred to as alcohol (4) used as a reaction substrate.

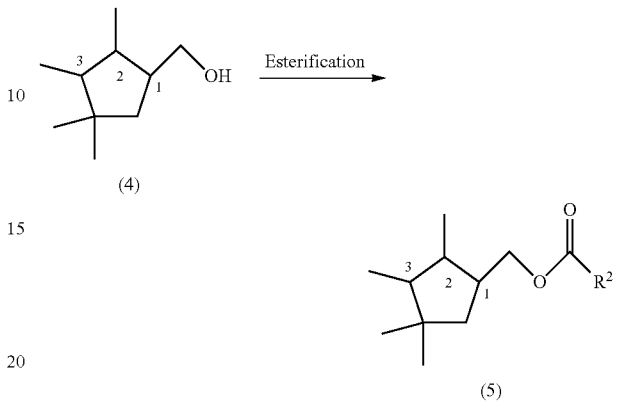

The esterification step may be carried out in any known ester formation method, for example, (i) a reaction with an acylating agent, (ii) a reaction with a carboxylic acid, (iii) a transesterification, and (iv) a process of converting an alcohol compound (4), which is a substrate, into an alkylating agent and then reacting it with a carboxylic acid.

(i) Reaction with an Acylating Agent

The reaction with an acylating agent may be carried out by reacting alcohol (4) used as a reaction substrate with an acylating agent and a base or acid in this order, in the reversed order, or simultaneously.

The reaction with an acylating agent may be carried out in the presence or absence of a solvent.

Examples of the solvent used in the reaction with an acylating agent include chlorinated solvents such as methylene chloride, chloroform, and trichloroethylene; hydrocarbons such as hexane, heptane, benzene, toluene, xylene, and cumene; ethers such as diethyl ether, di-n-butyl ether, diethyleneglycol diethyl ether, diethyleneglycol dimethyl ether, tetrahydrofuran, and 1,4-dioxane; nitriles such as acetonitrile; ketones such as acetone and 2-butanone; esters such as ethyl acetate and n-butyl acetate; and aprotic polar solvents such as N,N-dimethylformamide, dimethyl sulfoxide, and hexamethylphosphoric triamide.

The solvent may be used alone or in combination thereof, if necessary. The solvent may be commercially available one.

Examples of the acylating agent include carboxylic acid chlorides, carboxylic acid bromides, carboxylic acid anhydrides, mixed carboxylic/trifluoroacetic anhydride, mixed carboxylic/methanesulfonic anhydride, mixed carboxylic/trifluoromethanesulfonic anhydride, mixed carboxylic/benzensulfonic anhydride, mixed carboxylic/p-toluenesulfonic anhydride; and p-nitrophenyl carboxylate.

An amount of the acylating agent is from 0.8 mol to 500 mol, preferably from 0.8 mol to 50 mol, more preferably from 0.8 mol to 5 mol, per mol of alcohol (4) used as a reaction substrate.

Examples of the base preferably include triethylamine, diisopropylethylamine, N,N-dimethylaniline, pyridine, and 4-dimethylaminopyridine.

The reaction with the acylating agent such as an acid anhydride may be carried out in the presence of an acid catalyst instead of the base.

Examples of the acid catalyst include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium (IV) oxide.

An amount of the base or the acid catalyst is from 0.0001 mol to 500 mol, preferably from 0.001 mol to 50 mol, more preferably from 0.01 mol to 5 mol, per mol of alcohol (4) used as a reaction substrate.

A reaction temperature in the reaction with the acylating agent may be appropriately selected, depending on a type of the acylating agent and/or reaction conditions. Typically, the reaction temperature is preferably from −50° C. to a boiling point of the solvent, more preferably from −20° C. to 100° C.

A reaction time of the reaction with the acylating agent may be arbitrarily set. In view of the yield, it is desirable to monitor progress of the reaction with gas chromatography (GC) and/or silica gel thin layer chromatography (TLC) to complete the reaction. The reaction time is typically and preferably from 0.5 to 100 hours.

(ii) Reaction with a Carboxylic Acid

The reaction with a carboxylic acid is a dehydration condensation reaction between alcohol (4) used as a reaction substrate and a carboxylic acid and is typically carried out in the presence of an acid.

The carboxylic acid is represented by the general formula $R^2COOH$.

$R^2$ in the formula represents a hydrogen atom or a monovalent hydrocarbon group having 1 to 15, preferably 1 to 6 carbon atoms.

Examples of the monovalent hydrocarbon group of $R^2$ include linear saturated hydrocarbon groups such as a methyl group, an ethyl group, a propyl group, an n-butyl group, a hexyl group, and a pentadecyl group; branched saturated hydrocarbon groups such as an isopropyl group, an s-butyl group, an isobutyl group, a t-butyl group, and an isohexyl group; and linear alkenyl groups such as a vinyl group, an allyl group, a 2-methylallyl group, a 1-propenyl group, an isopropenyl group, a 1-methyl-1-propenyl group, and a 2-methyl-1-propenyl group. A part of the hydrogen atoms in the hydrocarbon group may be substituted with an acyl group having 1 to 6 carbon atoms, specifically a 1-acetoxy-2-methylpropyl group. Specific examples of the carboxylic acid include formic acid, acetic acid, propionic acid, butyric acid, valeric acid, heptanoic acid, hexadecanoic acid, isobutyric acid, isovaleric acid, pivalic acid, methylheptanoic acid, acrylic acid, vinylacetic acid, propenylacetic acid, crotonic acid, methacrylic acid, tiglic acid, senecioic acid, and 2-acetoxy-3-methylbutanoic acid.

An amount of the carboxylic acid is from 0.8 mol to 500 mol, preferably from 0.8 mol to 50 mol, more preferably from 0.8 mol to 5 mol, per mol of alcohol (4) used as a reaction substrate.

Example of the acid catalyst used in the reaction with a carboxylic acid include those used in the aforesaid (i) reaction with an acylating agent.

An amount of the acid catalyst is from 0.0001 mol to 100 mol, preferably from 0.001 mol to 1 mol, more preferably from 0.01 mol to 0.5 mol, per mol of alcohol (4) used as a reaction substrate. Example of the solvent used in the reaction between alcohol (4) used as a reaction substrate and a carboxylic acid include those used in the reaction with an acylating agent.

A reaction temperature in the reaction with a carboxylic acid may be appropriately selected, depending on a species of the carboxylic acid and/or reaction conditions. Typically, the reaction temperature is preferably from −50° C. to a boiling point of the solvent, more preferably from room temperature to a boiling point of the solvent. The reaction may be done in a solvent such as a hydrocarbon, such as hexane, heptane, benzene, toluene, xylene, or cumene, while removing the resulting water out of the system by azeotropic distillation. Alternatively, water may be distilled off with refluxing at the boiling point of the solvent in normal pressure or at a lower temperature than the boiling point of water in a reduced pressure.

A reaction time of the reaction with a carboxylic acid may be arbitrarily set. In view of the yield, it is desirable to monitor progress of the reaction with gas chromatography (GC) and/or silica gel thin layer chromatography (TLC) to complete the reaction. The reaction time is typically and preferably from 1 to 200 hours.

An alternative to the reaction with a carboxylic acid may be also carried out by subjecting a carboxylic acid to a condensation reaction with a condensing agent and then subjecting the condensation reaction product to a condensation reaction with alcohol (4) used as a reaction substrate in a basic condition.

An amount of the carboxylic acid used in the alternative is from 0.8 mol to 500 mol, preferably from 0.8 mol to 50 mol, more preferably from 0.8 mol to 5 mol, per mol of alcohol (4) used as a reaction substrate.

Examples of the condensing agent include carbodiimides such as N,N'-dicyclohexylcarbodiimide (DCC), N,N'-diisopropylcarbodiimide (DIC), 1-ethyl-3-(3-dimethylaminopropyl)-carbodiimide (EDC), and 1-ethyl-3-(3-dimethylaminopropyl)-carbodiimide hydrochloride (EDC-HCl); and uronium salts such as O-(7-aza-1H-benzotriazol-1-yl)-N,N,N',N'-tetramethyluronium hexafluorophosphate (HATU) and O-(benzotriazol-1-yl)-N,N,N',N'-tetramethyluronium hexafluorophosphate (HBTU).

The condensing agent may be used alone or in combination thereof, if necessary. The condensing agent may be commercially available one.

An amount of the condensing agent is from 0.8 mol to 500 mol, preferably from 0.8 mol to 50 mol, more preferably from 0.8 mol to 5 mol, per mol of alcohol (4) used as a reaction substrate. Examples of the base include triethylamine, diisopropylethylamine, N,N-dimethylaniline, pyridine, and 4-dimethylaminopyridine.

The solvent used in the alternative may be same as that used in the reaction with an acylating agent.

A reaction temperature in the alternative may be appropriately selected, depending on a species of the carboxylic acid and/or reaction conditions. Typically, the reaction temperature is preferably from −50° C. to a boiling point of the solvent, more preferably from room temperature to a boiling point of the solvent.

A reaction time of the alternative may be arbitrarily set. In view of the yield, it is desirable to monitor progress of the reaction with gas chromatography (GC) and/or silica gel thin layer chromatography (TLC) to complete the reaction. The reaction time is typically and preferably from 0.5 to 100 hours.

(iii) Transesterification

The transesterification is carried out by reacting alcohol (4) used as a reaction substrate with an alkyl carboxylate ($R^2$COOR) in the presence of a reaction catalyst while removing a formed alkyl alcohol (ROH), as shown in the following reaction formula.

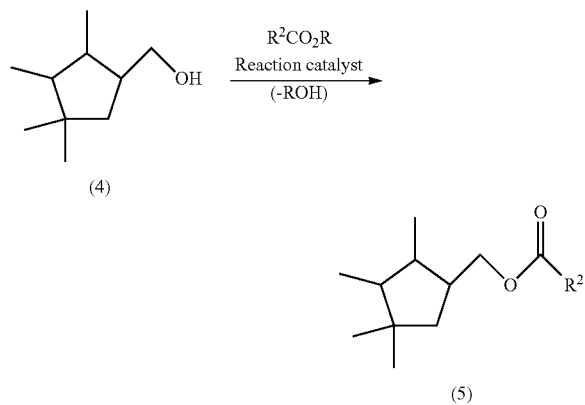

wherein R represents an alkyl group, and $R^2$ is as defined above.

The alkyl carboxylate is preferably a primary alkyl ester of a carboxylic acid. A methyl carboxylate ($R^2$COOCH$_3$), an ethyl carboxylate ($R^2$COOCH$_2$CH$_3$), and an n-propyl carboxylate ($R^2$COOCH$_2$CH$_2$CH$_3$) are particularly preferred in view of the price and/or easier progress of the reaction.

$R^2$ in the general formula representing the primary alkyl ester of a carboxylic acid is as defined for $R^2$ in the general formula $R^2$COOH in the aforesaid (ii) reaction with a carboxylic acid.

An amount of the alkyl carboxylate is from 0.8 mol to 500 mol, preferably from 0.8 mol to 50 mol, more preferably from 0.8 mol to 5 mol, per mol of alcohol (4) used as a reaction substrate.

Examples of the catalyst used in the transesterification include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; bases such as sodium methoxide, sodium ethoxide, potassium t-butoxide, and 4-dimethylaminopyridine; salts such as sodium cyanide, potassium cyanide, sodium acetate, potassium acetate, calcium acetate, tin acetate, aluminum acetate, aluminum acetoacetate, and alumina; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide.

The catalyst may be used alone or in combination thereof, if necessary. The catalyst may be commercially available one.

An amount of the catalyst is from 0.0001 mol to 100 mol, preferably from 0.001 mol to 1 mol, more preferably 0.001 mol to 0.05 mol which are a catalytic amount, per mol of alcohol (4) used as a reaction substrate.

Examples of the solvent used in the transesterification include hydrocarbons such as hexane, heptane, benzene, toluene, xylene, and cumene; and ethers such as diethyl ether, di-n-butylether, diethyleneglycol diethyl ether, diethyleneglycol dimethyl ether, tetrahydrofuran, and 1,4-dioxane.

The solvent may be used alone or in combination thereof, if necessary. The solvent may be commercially available one.

Depending on a condition of the transesterification, the reaction may be carried out without a solvent wherein the alkyl carboxylate works as a solvent. This is advantageous in that any extra operation, such as concentration and/or solvent recovery, is unnecessary.

A reaction temperature in the transesterification may be appropriately selected, depending on a species of the alkyl carboxylate and/or reaction conditions. The transesterification is typically carried out under heating around a boiling point of a lower alcohol generated in the transesterification, such as methanol, ethanol, or 1-propanol, and is successfully carried out while distilling the formed lower alcohol off. The alcohol may be distilled off at a lower temperature under reduced pressure.

A reaction time of the transesterification may be arbitrarily set. In view of the yield, it is desirable to monitor progress of the reaction with gas chromatography (GC) and/or silica gel thin layer chromatography (TLC) to complete the reaction. The reaction time is typically and preferably from 1 to 200 hours.

(iv) Process of Converting Alcohol (4) Used as a Reaction Substrate into an Alkylating Agent and then Reacting it with a Carboxylic Acid The process of converting alcohol (4) used as a reaction substrate into an alkylating agent and then reacting it with a carboxylic acid may be carried out by, for example, converting alcohol (4) used as a reaction substrate into a corresponding halide (a chloride, a bromide, or an iodide) or sulfonate (for example, methansulfonate, trifluoromethanesulfonate, benzenesulfonate, or p-toluenesulfonate) and then reacting the corresponding halide with a carboxylic acid typically in a solvent in a basic condition. The reaction may be also carried out by mixing alcohol (4) used as a reaction substrate with triphenylphosphine and diethyl azodicarboxylate and then reacting the mixture with a carboxylic acid typically in a solvent.

The carboxylic acid may be same as that used in the aforesaid (ii) reaction with a carboxylic acid.

A solvent, a base, a reaction time, and a reaction temperature to be used may be same as those used in the reaction of alcohol (4) used as a reaction substrate with an acylating agent. Instead of the combination of a carboxylic acid and a base, a carboxylate salt such as sodium carboxylate, lithium carboxylate, potassium carboxylate, or ammonium carboxylate may be used.

The (2,3,4,4-tetramethylcyclopentyl)methyl carboxylate compound (5) thus prepared may be isolated and/or purified in any purification method used in ordinary organic syntheses, such as distillation under reduced pressure and/or various chromatography. Distillation under reduced pressure is preferred in view of the industrial economy.

Before the reduction reaction step, 2,3,4,4-tetramethylcyclopentanecarbaldehyde (3) may be subjected to an isomerization reaction.

The isomerization step is optional and may be carried out when trans selectivity of the substituents at positions 1 and 2 is required to be increased.

One embodiment of the isomerization step includes the following chemical reaction formula.

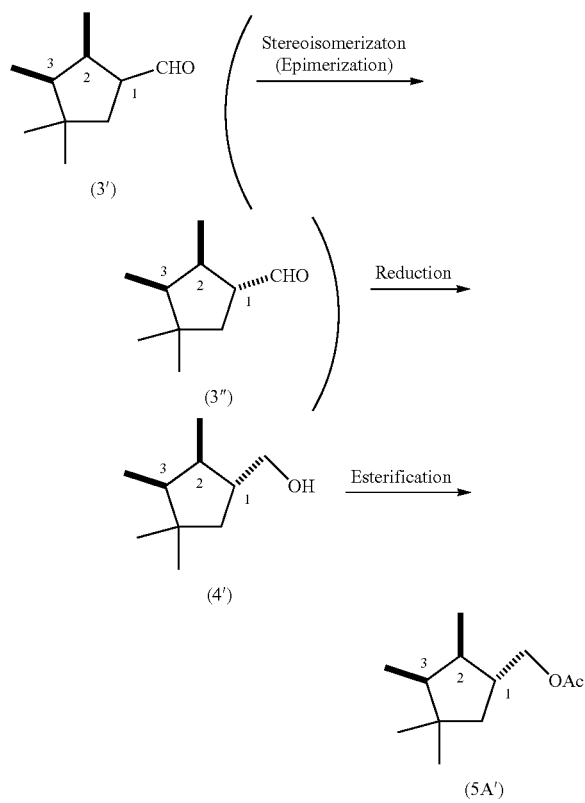

The chemical reaction aims to selectively synthesize (1R*,2R*,3S*)-(2,3,4,4-tetramethylcyclopentyl)methyl acetate (5A'), which is a racemic mixture of the sex pheromone of OMB, among the target compounds (2,3,4,4-tetramethylcyclopentyl)methyl carboxylate compounds (5) by using as a starting material the (1R*,2R*,3S*)-form (3') instead of 2,3,4,4-tetramethylcyclopentanecarbaldehyde (3), via the (1R*,2R*,3S*)-form (3").

Specifically, the chemical reaction comprises steps of subjecting (1RS,2R*,3S*)-2,3,4,4-tetramethylcyclopentanecarbaldehyde (3') to an isomerization reaction to form (1R*,2R*,3S*)-2,3,4,4-tetramethylcyclopentanecarbaldehyde (3"), subjecting (1R*,2R*,3S*)-2,3,4,4-tetramethylcyclopentanecarbaldehyde (3") thus prepared to a reduction reaction with a reducing agent to form (1R*,2R*,3S*)-(2,3,4,4-tetramethylcyclopentyl)methanol (4'), and subjecting (1R*,2R*,3S*)-(2,3,4,4-tetramethylcyclopentyl)methanol (4') thus prepared to an esterification reaction to form (1R*,2R*,3S*)-(2,3,4,4-tetramethylcyclopentyl)methyl acetate (5A'). As mentioned above, the isomerization reaction is optional, and thus (1RS,2R*,3S*)-2,3,4,4-tetramethylcyclopentanecarbaldehyde (3') may be directly subjected to a reduction reaction without the isomerization reaction.

The isomerization step may be carried out, for example, by processing the substrate (1RS,2R*,3S*)-form (3') in an acidic or basic condition. The aldehyde group at position 1 of the (1RS,2R*,3S*)-form (3') may be stereoisomerized in an acidic or basic condition via the equilibrium between the enol form and the aldehyde form to convergently provide a thermodynamically more stable configuration. Therefore, it is expected that the abundance ratio of the 1,2-trans form that has less steric repulsion between the substituents at positions 1 and 2 increases to give the (1R*,2R*,3S*)-form (3").

The isomerization reaction may be carried out by mixing the substrate and an acid or a base, if necessary, in a solvent. The isomerization reaction may be carried out with cooling or heating.

An acid suitably used in the isomerization reaction in an acidic condition and an amount of the acid may be same as those used in the hydrolysis reaction in step B.

The base suitably used in the isomerization reaction in a basic condition may be same as that used in the preparation step of the phosphorus ylide compound (7) in step A.

An amount of the base may be arbitrarily set as long as a practically sufficient reaction rate is achieved. The amount is preferably from 0.00001 to 10,000 mol, more preferably from 0.0001 to 1,000 mol, even more preferably from 0.001 to 100 mol, per mol of the substrate 2,3,4,4-tetramethylcyclopentanecarbaldehyde (3).

A solvent that may be incorporated in the isomerization reaction and an amount of the solvent, a reaction temperature, and a reaction time may be same as those used in the hydrolysis reaction in step B.

When the (1R*,2R*,3S*)-form (3") obtained in the isomerization reaction has a sufficient purity for a subsequent step, a crude product or a reaction mixture or a reaction mixture filtrate may be used as such in the subsequent step. Alternatively, when it is desired to separate and remove impurities, they may be removed in any purification method used in ordinary organic syntheses, such as distillation and/or various chromatography. The purification is preferably distillation, for example distillation under reduced pressure, in view of the industrial economy.

The isomerization reaction is a reason to allow the preparation of (1R*,2R*,3S*)-(2,3,4,4-tetramethylcyclopentyl)methyl acetate (5A') in a diastereomeric ratio, dr, of 50% or more.

Next, the (1R*,2R*,3S*)-form (3") thus prepared is subjected to a reduction reaction with a reducing agent to form (1R*,2R*,3S*)-(2,3,4,4-tetramethylcyclopentyl)methanol (4').

Finally, (1R*,2R*,3S*)-(2,3,4,4-tetramethylcyclopentyl)methanol (4') thus prepared is subjected to esterification to form (1R*,2R*,3S*)-(2,3,4,4-tetramethylcyclopentyl)methyl acetate (5A') which is a racemic mixture of the sex pheromone of OMB.

(1R*,2R*,3S*)-(2,3,4,4-Tetramethylcyclopentyl)methanol (4') prepared in a diastereomeric ratio of 50% dr or more allows the preparation of (1R*,2R*,3S*)-(2,3,4,4-tetramethylcyclopentyl)methyl acetate (5A') in a diastereomeric ratio, dr, of 50% or more.

The preparation process of the present invention makes it possible to prepare stereoselectively and easily the (1R*,2R*,3S*)-form (5A') having the relative configuration same as that of the naturally occurring sex pheromone of OMB in a selectivity of 50% dr or more, among four diastereomers of (2,3,4,4-tetramethylcyclopentyl)methyl acetate corresponding to the 2-dimensional structural formula of the sex pheromone of OMB. Adjusting the reaction conditions allows 60% dr or more, 70% dr or more, 80% or more, and even 90% or more.

EXAMPLES

The present invention will be described with reference to the following Examples. It should be noted that the present invention is not limited to or by the Examples.

The term "purity" as used herein means an area percentage in gas chromatography (GC), unless otherwise specified. The term "product ratio" means a ratio of area percentages in GC.

The term "yield" is calculated from the area percentages determined by GC.

In the Examples, monitoring of the reactions and calculation of the yields were carried out essentially in the following GC conditions.

GC conditions: GC equipment: SHIMADZU GC-2014, capillary column: DB-5, 0.25 mm in internal diameter×0.25 μm in thickness×30 m in length, carrier gas: He, detector: FID, column temperature: elevated from 80° C. in a rate of +5° C./minute, inlet temperature: 230° C.

Purities of raw materials, products, and intermediates were determined by gas chromatography (GC) and expressed as % GC.

The yield was calculated according to the following equation in consideration of purities (% GC) of a starting material and a product.

Yield (%)={[(weight of a product obtained by a reaction×% GC)/molecular weight of a product]: [(weight of a starting material in a reaction×% GC)/molecular weight of a starting material]}×100

The term "crude yield" refers to a yield of a crude product obtained without purification.

A sample for measuring the spectrum was obtained by purifying a crude product, if necessary.

In the following chemical structure, Me represents a methyl group, Ph represents a phenyl group, and Ac represents an acetyl group.

Example 1: Synthesis of 4-(methoxymethylene)-1,1,2,3-tetramethyl-2-cyclopentene (1A)

(1: $R^1$=methyl group)

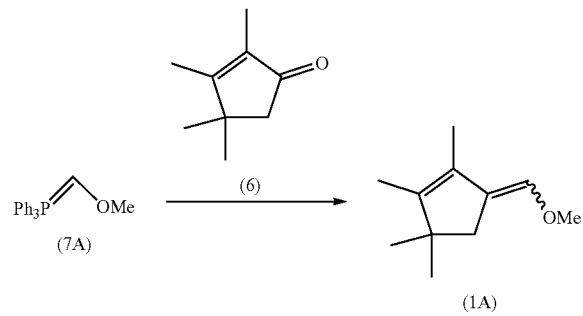

To a mixture of potassium tert-butoxide (183 g) and tetrahydrofuran (847 g) was added (methoxymethyl)triphenylphosphonium chloride (588 g) under nitrogen atmosphere with ice-cooling and stirring and stirred for 100 minutes to prepare phosphorus ylide (7A) (7: $R^1$=methyl group). A mixture of 2,3,4,4-tetramethyl-2-cyclopenten-1-one (6) (121 g, 98.0% GC) and tetrahydrofuran (480 g) was added and stirred overnight. After distilling off the solvent, the soluble part was extracted with hexane, and the hexane was distilled off to obtain a crude product. The crude product was purified by distillation under reduced pressure to obtain 4-(methoxymethylene)-1,1,2,3-tetramethyl-2-cyclopentene (1A) (116 g, 98.3% GC, yield 80%) as a mixture of geometric isomers showing geometrical isomerism regarding the exocyclic double bond (product ratio: E-form/Z-form=75/25) (boiling point: 73 to 75° C./1.0 kPa).

4-(Methoxymethylene)-1,1,2,3-tetramethyl-2-cyclopentene (1A)

Yellowish oil.

IR (D-ATR): ν=2954, 2928, 2862, 2830, 1705, 1668, 1461, 1376, 1358, 1328, 1251, 1223, 1135, 1090, 982, 802 cm$^{-1}$ $^1$H-NMR (500 MHZ, CDCl$_3$):

Major isomer (E-form): δ=0.96 (6H, s), 1.54 (3H, s), 1.58 (3H, d, J=0.8 Hz), 2.21 (2H, d, J=2.3 Hz), 3.53 (3H, s), 5.98 (1H, tq, J=2.3, 0.8 Hz) ppm.

Minor isomer (Z-form): δ=0.93 (6H, s), 1.54 (3H, s), 1.79 (3H, d, J=0.8 Hz), 2.13 (2H, d, J=1.5 Hz), 3.44 (3H, s), 5.76 (1H, tq, J=1.5, 0.8 Hz) ppm.

$^{13}$C-NMR (126 MHz, CDCl$_3$): a mixture of E/Z geometric isomers, δ=9.40, 9.64, 10.08, 13.16, 26.62, 27.25, 41.28, 42.58, 43.81, 44.41, 59.08, 59.40, 122.26, 125.01, 127.56, 129.18, 136.64, 137.01, 143.19, 145.38 ppm.

GC-MS (EI, 70 eV): 29, 41, 53, 65, 77, 91, 105, 119, 136, 151, 166 (M+).

Example 2: Synthesis of 2,3,4,4-tetramethyl-1-cyclopentenecarbaldehyde (2)

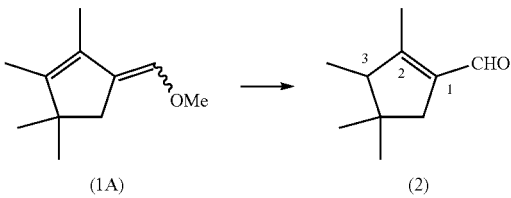

A mixture of 4-(methoxymethylene)-1,1,2,3-tetramethyl-2-cyclopentene (1A) obtained according to Example 1 (20.0 g, 98.3% GC), hexane (40 g), tetrahydrofuran (40 g), and 20% hydrochloric acid (65 g) was stirred under nitrogen atmosphere for 6 hours. The organic layer was separated and then subjected to work-up process, i.e., ordinary washing, and concentration, to obtain a crude product. The crude product was purified by distillation under reduced pressure to obtain 2,3,4,4-tetramethyl-1-cyclopentenecarbaldehyde (2) (11.7 g, 95.1% GC, yield 62%) (boiling point 61° C./0.45 kPa).

2,3,4,4-Tetramethyl-1-cyclopentenecarbaldehyde (2)

Brownish oil.

IR (D-ATR): ν=2960, 2869, 2719, 1663, 1633, 1440, 1377, 1340, 1256, 1228, 1210 cm$^{-1}$.

$^1$H-NMR (500 MHZ, CDCl$_3$): δ=1.03 (3H, s), 0.97 (3H, d, J=7.7 Hz), 8.72 (3H, s), 2.06 (3H, m), 2.25 (1H, m, *including d, J=15.6 Hz), 2.32 (1H, m, *including d, J=15.6 Hz), 2.35 (1H, m, *including q, J=7.7 Hz), 9.98 (1H, s) ppm.

$^{13}$C-NMR (126 MHz, CDCl$_3$): δ=11.86, 12.88, 23.25, 28.65, 39.89, 43.28, 55.53, 136.41, 165.40, 188.70 ppm.

GC-MS (EI, 70 eV): 27, 41, 55, 67, 81, 95, 109, 123, 137, 152 (M+).

Example 3: Synthesis of 2,3,4,4-tetramethylcyclopentanecarbaldehyde (3) ((1RS,2R*,3S*)-2,3,4,4-tetramethylcyclopentanecarbaldehyde (3') and (1RS,2R*,3R*)-2,3,4,4-tetramethylcyclopentanecarbaldehyde)

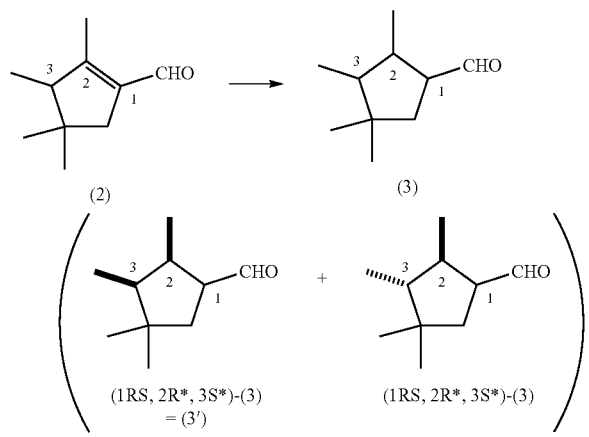

In an autoclave were placed 2,3,4,4-tetramethyl-1-cyclopentenecarbaldehyde (2) obtained according to Example 2 (11.3 g, 88.4% GC), hexane (136 g), and 5% rhodium on carbon (1.35 g), and the autoclave was filled with hydrogen gas, followed by stirring for 20 hours. The solid content was filtered off, and then the solvent was distilled off to obtain 2,3,4,4-tetramethylcyclopentanecarbaldehyde (3) (12.0 g, 71.3% GC, crude yield 85%) as a crude product. The product ratio of the (1RS,2R*,3S*)-form (3') (having the same relative configuration as that of the sex pheromone of OMB at positions 2 and 3)/the (1RS,2R*,3R*)-form (having a different relative configuration from that of the sex pheromone of OMB at positions 2 and 3) was determined to be 96/4 by GC. The (1RS,2R*,3S*)-form (3') had a GC purity of 68.7% GC and a crude yield of 82%.

2,3,4,4-Tetramethylcyclopentanecarbaldehyde (3)

Yellowish oil.
IR (D-ATR): ν=2959, 2872, 2707, 1723, 1663, 1456, 1379 cm$^{-1}$.
GC-MS (EI, 70 eV): 29, 41, 55, 69, 83, 97, 98, 109, 123, 139, 154 (M+).

Example 4: Synthesis of (1R*,2R*,3S*)-(2,3,4,4-tetramethylcyclopentyl)methanol (4')

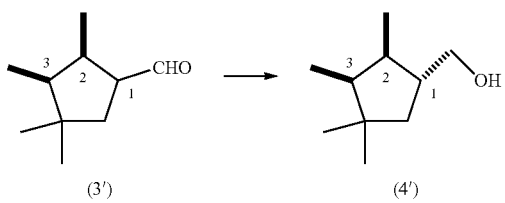

A mixture of (1RS,2R*,3S*)-2,3,4,4-tetramethylcyclopentanecarbaldehyde (3') obtained according to Example 3 (12.0 g, 68.7% GC), tetrahydrofuran (50 g), an aqueous solution of 5% sodium hydroxide (22 g) was stirred under nitrogen atmosphere for 40 hours, and an aqueous solution of 10% sodium borohydride (10.1 g) was then added and stirred for additional 2 hours. The reaction mixture was diluted with hexane. The organic layer was separated and then subjected to work-up process, i.e., ordinary washing and concentration, to obtain a crude product. The crude product was purified by distillation under reduced pressure to obtain (1R*,2R*,3S*)-(2,3,4,4-tetramethylcyclopentyl)methanol (4') (6.95 g, 88.0% GC, yield 73%) (boiling point 91 to 92° C./1.0 kPa).

(1R*,2R*,3S*)-(2,3,4,4-Tetramethylcyclopentyl)methanol (4')

Colorless oil.
IR (D-ATR): ν=3329 (broad), 2955, 2872, 1459, 1386, 1377, 1053, 1005 cm$^{-1}$.
$^{1}$H-NMR (500 MHZ, CDCl$_3$): δ=0.78 (3H, d, J=7.3 Hz), 0.86 (3H, s), 0.95 (3H, d, J=6.9 Hz), 0.97 (3H, s), 1.16 (1H, dd, J=12.2, 9.6 Hz), 1.61 (1H, br.s), 1.64 (1H, dq, J=9.2, 7.3 Hz), 1.68 (1H, dd, J=12.6, 8.0 Hz), 1.81 (1H, m), 1.88 (1H, m), 3.52 (1H, dd, J=10.3, 7.3 Hz), 3.66 (1H, dd, J=10.3, 5.4 Hz) ppm.
$^{13}$C-NMR (126 MHz, CDCl$_3$): δ=10.24, 17.43, 23.86, 29.78, 38.62, 41.33, 44.50, 46.19, 48.20, 67.47 ppm.
GC-MS (EI, 70 eV): 29, 41, 55, 69, 82, 97, 109, 123, 141, 154 (M+).

Example 5: Synthesis of (1R*,2R*,3S*)-(2,3,4,4-tetramethylcyclopentyl)methyl acetate (5A')

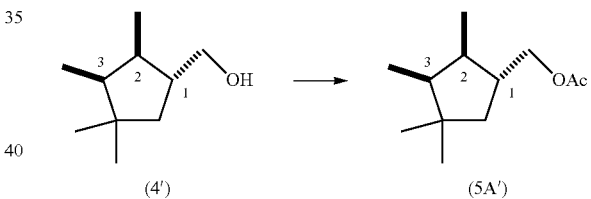

A mixture of (1R*,2R*,3S*)-(2,3,4,4-tetramethylcyclopentyl)methanol (4') obtained according to Example 4 (6.45 g, 88.0% GC), pyridine (7.20 g), and acetic anhydride (6.30 g) was stirred under nitrogen atmosphere for 4 hours. Water and hexane were added, and the organic layer was separated and then subjected to work-up process, i.e., ordinary washing and concentration, to obtain a crude product. The crude product was purified by distillation under reduced pressure to obtain (1R*,2R*,3S*)-(2,3,4,4-tetramethylcyclopentyl)methyl acetate (5A') (7.48 g, 88.6% GC, yield 92%) (boiling point 87° C./0.87 kPa).
The diastereomeric ratio of (1R*,2R*,3S*)-(2,3,4,4-tetramethylcyclopentyl)methyl acetate (5A') having the relative configuration same as that of the sex pheromone of OMB was determined to be 92.8% dr by GC. (1R*,2R*,3S*)-(2,3,4,4-Tetramethylcyclopentyl)methyl acetate (5A')
Colorless oil.
IR (D-ATR): ν=2957, 2873, 1743, 1458, 1367, 1242, 1042, 970 cm$^{-1}$.
$^{1}$H-NMR (500 MHz, CDCl$_3$): δ=0.78 (3H, d, J=7.3 Hz), 0.85 (3H, s), 0.95 (3H, d, J=6.9 Hz), 0.97 (3H, s), 1.15 (1H, dd, J=12.6, 9.2 Hz), 1.65 (1H, dq, J=8.7, 7.3 Hz), 1.67 (1H, dd, J=12.6, 7.6 Hz), 1.87-1.97 (2H, m), 2.05 (3H, s), 3.99 (1H, dd, J=10.7, 6.9 Hz), 4.06 (1H, dd, J=10.7, 5.8 Hz) ppm.

$^{13}$C-NMR (126 MHz, CDCl$_3$): δ=10.22, 17.14, 21.02, 23.84, 29.73, 39.11, 41.28, 44.49, 44.52, 46.21, 68.76, 171.35 ppm.

GC-MS (EI, 70 eV): 29, 43, 55, 69, 82, 97, 109, 123, 138, 154, 165, 178, 192.

Example 6: Synthesis of (2,3,4,4-tetramethylcyclopentyl)methyl acetate (5A)

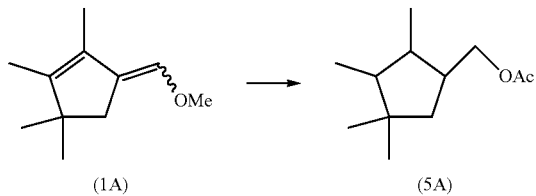

In an autoclave were placed the crude product 2,3,4,4-tetramethyl-1-cyclopentenecarbaldehyde (2) obtained according to Example 2 (6.84 g, 78.0% GC, crude yield 88.9%), tetrahydrofuran (27 g), and 5% palladium on carbon (0.38 g), and the autoclave was filled with hydrogen gas, followed by stirring for 18 hours. The solid content was filtered off, and then an aqueous solution of 5% sodium hydroxide (15.4 g) was added and stirred under nitrogen atmosphere for 18 hours. An aqueous solution of 10% sodium borohydride (7.3 g) was added to the reaction mixture and stirred for 3 hours. The reaction mixture was diluted with hexane, and the organic layer was separated and then subjected to work-up process, i.e., ordinary washing and concentration, to obtain a crude product (2,3,4,4-tetramethylcyclopentyl)methanol (4). Subsequently, pyridine (7.59 g) and acetic anhydride (5.88 g) were added and stirred under nitrogen atmosphere for 5 hours. After the completion of the stirring, water and hexane were added, and the organic layer was separated and then subjected to work-up process, i.e., ordinary washing and concentration, to obtain a crude product. The crude product was purified by distillation under reduced pressure to obtain (2,3,4,4-tetramethylcyclopentyl)methyl acetate (5A) (5.87 g, 90.4% GC) (boiling point 92 to 96° C./1.1 kPa).

The crude product was obtained in a yield of 68% from 4-(methoxymethylene)-1,1,2,3-tetramethyl-2-cyclopentene (1A) and in an overall yield of 55% from 2,3,4,4-tetramethyl-2-cyclopenten-1-one (6).

The diastereomeric ratio of (1R*,2R*,3S*)-(2,3,4,4-tetramethylcyclopentyl)methyl acetate (5A') having the relative configuration same as that of the sex pheromone of OMB was determined to be 78.1% dr by GC.

(2,3,4,4-Tetramethylcyclopentyl)methyl acetate (5A)

Colorless oil.

IR (D-ATR): ν=2956, 2872, 1743, 1455, 1366, 1242, 1042, 970 cm-1

$^1$H-NMR (500 MHZ, CDCl$_3$): major isomer, δ=0.78 (3H, d, J=7.3 Hz), 0.85 (3H, s), 0.95 (3H, d, J=6.9 Hz), 0.97 (3H, s), 1.15 (1H, dd, J=12.6, 9.2 Hz), 1.65 (1H, dq, J=8.7, 7.3 Hz), 1.67 (1H, dd, J=12.6, 7.6 Hz), 1.87-1.97 (2H, m), 2.05 (3H, s), 3.99 (1H, dd, J=10.7, 6.9 Hz), 4.06 (1H, dd, J=10.7, 5.8 Hz) ppm.

$^{13}$C-NMR (126 MHz, CDCl$_3$): major isomer, δ=10.22, 17.14, 21.02, 23.84, 29.73, 39.11, 41.28, 44.49, 44.52, 46.21, 68.76, 171.35 ppm.

GC-MS (EI, 70 eV): 29, 43, 55, 69, 82, 97, 109, 123, 138, 154, 165, 178, 192.

Comparative Synthetic Example: Synthesis of (2S*,3S*)-4-(methoxymethylene)-1,1,2,3-tetramethylcyclopentane (104) from (2R*,3S*)-2,3,4,4-tetramethyl-2-cyclopenten-1-one (103)

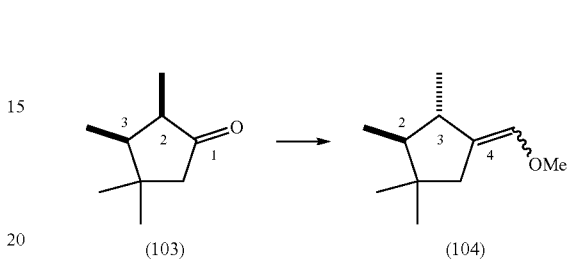

To a mixture of (methoxymethyl)triphenylphosphonium chloride (4.46 g) and tetrahydrofuran (10 g) was added potassium tert-butoxide (1.35 g) under nitrogen atmosphere with ice-cooling and stirring. The mixture was stirred for 20 minutes, and then a mixture of (2R*,3S*)-2,3,4,4-tetramethyl-2-cyclopenten-1-one (103) (1.50 g, 85.6% GC) and toluene (10 g) was added. The temperature of the mixture was raised to room temperature, and the mixture was stirred for 10 hours. Water and diethyl ether were added, and the organic layer was separated and then subjected to work-up process, i.e., separation, washing, filtration, drying, and concentration, to obtain 4-(methoxymethylene)-1,1,2,3-tetramethylcyclopentane as a crude product (1.41 g, 75.8% GC, crude yield 63.5%).

The product thus prepared was the (2S*,3S*)-form (104) formed by subjecting the methyl group at position 2 of the substrate (2R*,3S*)-2,3,4,4-tetramethyl-2-cyclopenten-1-one (103) to epimerization followed by a Wittig reaction. The (2S*,3R*)-form (104') having the relative configuration same as that of the sex pheromone of OMB was not confirmed to be present by GC-MS analysis.

The confirmation of the relative configuration was carried out by processing the reaction product in a similar manner to Examples 2, 4, and 5, converting the resulting product into (2,3,4,4-tetramethylcyclopentyl)methyl acetate (5A), and comparing the observed data with the physical property data described in Non-Patent Literature 3.

INDUSTRIAL APPLICABILITY

The results indicate that the preparation process of the present invention makes it possible to prepare safely, efficiently, selectively, and industrially a (2,3,4,4-tetramethylcyclopentyl)methyl carboxylate compound, particularly (1R*,2R*,3S*)-(2,3,4,4-tetramethylcyclopentyl)methyl acetate, which is used as the sex pheromone of an serious agricultural pest, OMB, and is promising for applications such as forecasting outbreaks of the pest and controlling the pest, as compared with known methods and are highly valuable for industrial applications.

The invention claimed is:

1. A process for preparing 2,3,4,4-tetramethyl-1-cyclopentenecarbaldehyde of the following formula (2), the process comprising subjecting a vinylether compound of the following general formula (1) to a hydrolysis reaction to form 2,3,4,4-tetramethyl-1-cyclopentenecarbaldehyde (2)

(1)

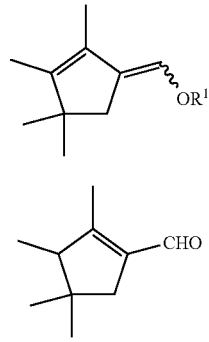

(2)

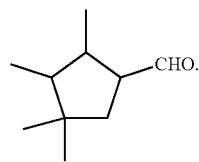

wherein in the general formula (1), R¹ represents a monovalent hydrocarbon group having 1 to 15 carbon atoms, and the wavy line represents the E-form, the Z-form, or a mixture thereof.

2. A process for preparing 2,3,4,4-tetramethylcyclopentanecarbaldehyde of the following formula (3), the process comprising:

the process according to claim 1 for preparing 2,3,4,4-tetramethyl-1-cyclopentenecarbaldehyde (2), and subjecting 2,3,4,4-tetramethyl-1-cyclopentenecarbaldehyde (2) thus obtained to a hydrogenation reaction to form 2,3,4,4-tetramethylcyclopentanecarbaldehyde (3)

(3)

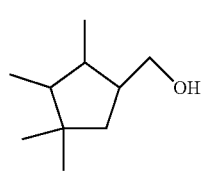

3. The process for preparing a (2,3,4,4-tetramethylcyclopentyl)methyl carboxylate compound of the following general formula (5), the process comprising:

the process according to claim 2 for preparing 2,3,4,4-tetramethylcyclopentanecarbaldehyde (3), subjecting 2,3,4,4-tetramethylcyclopentanecarbaldehyde (3) thus obtained to a reduction reaction with a reducing agent to form (2,3,4,4-tetramethylcyclopentyl)methanol of the following formula (4), and subjecting (2,3,4,4-tetramethylcyclopentyl)methanol (4) thus obtained to an esterification reaction to form the (2,3,4,4-tetramethylcyclopentyl)methyl carboxylate compound (5)

(4)

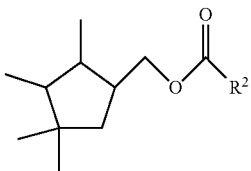

(5)

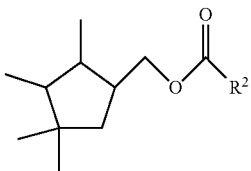

wherein in the general formula (5), R² represents a hydrogen atom or a monovalent hydrocarbon group having 1 to 15 carbon atoms.

4. The process for preparing the (2,3,4,4-tetramethylcyclopentyl)methyl carboxylate compound (5) according to claim 3, wherein the carboxylate compound (5) is (2,3,4,4-tetramethylcyclopentyl)methyl acetate of the following formula (5A) and comprises (1R*,2R*,3S*)-(2,3,4,4-tetramethylcyclopentyl)methyl acetate of the following formula (5A') in a diastereomeric ratio, dr, of 50% or more among four diastereomers of (2,3,4,4-tetramethylcyclopentyl)methyl acetate (5A)

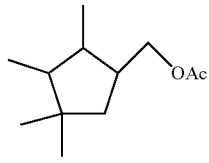

(5A')

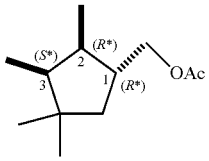

wherein in the formulae (5A) and (5A'), Ac represents an acetyl group, and (R*), (S*), the bold bond, and the hashed bond represents a relative configuration.

5. The process according to claim 4, wherein 2,3,4,4-tetramethylcyclopentanecarbaldehyde (3) is as (1RS,2R*,3S*)-2,3,4,4-tetramethylcyclopentanecarbaldehyde of the following formula (3'), the process further comprising subjecting (1RS,2R*,3S*)-2,3,4,4-tetramethylcyclopentanecarbaldehyde (3') to an isomerization reaction to form (1R*,2R*,3S*)-2,3,4,4-tetramethylcyclopentanecarbaldehyde of the following formula (3");

wherein the reduction reaction is carried out on (1R*,2R*,3S*)-2,3,4,4-tetramethylcyclopentanecarbaldehyde (3") thus obtained to form (1R*,2R*,3S*)-(2,3,4,4-tetramethylcyclopentyl)methanol (4'); and wherein the esterification reaction is carried out on (1R*,2R*,3S*)-(2,3,4,4-tetramethylcyclopentyl)methanol (4') thus obtained to form (1R*,2R*,3S*)-(2,3,4,4-tetramethylcyclopentyl)methyl acetate (5A')

(3')

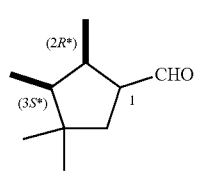

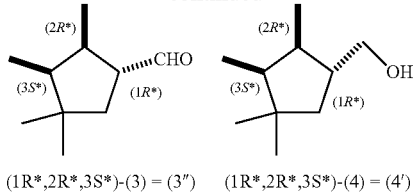

(1R*,2R*,3S*)-(3) = (3″)   (1R*,2R*,3S*)-(4) = (4′)

wherein the bold bond and the hashed bond represents a relative configuration.

6. The process for preparing 2,3,4,4-tetramethyl-1-cyclopentenecarbaldehyde (2) according to claim 1, the process further comprising subjecting 2,3,4,4-tetramethyl-2-cyclopentenone of the following formula (6) to a Wittig reaction with a phosphorus ylide compound of the following general formula (7) to form the vinylether compound (1)

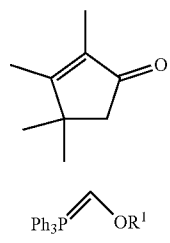 (6)

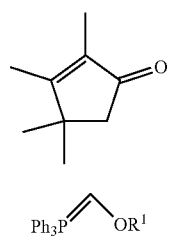 (7)

wherein, in the general formula (7), R¹ represents a monovalent hydrocarbon group having 1 to 15 carbon atoms, and Ph represents a phenyl group.

7. The process for preparing 2,3,4,4-tetramethylcyclopentanecarbaldehyde (3) according to claim 2, the process further comprising subjecting 2,3,4,4-tetramethyl-2-cyclopentenone of the following formula (6) to a Wittig reaction with a phosphorus ylide compound of the following general formula (7) to form the vinylether compound (1)

(6)

(7)

wherein, in the general formula (7), R¹ represents a monovalent hydrocarbon group having 1 to 15 carbon atoms, and Ph represents a phenyl group.

8. The process according to claim 3 for preparing the (2,3,4,4-tetramethylcyclopentyl)methyl carboxylate compound (5), the process further comprising subjecting 2,3,4,4-tetramethyl-2-cyclopentenone of the following formula (6) to a Wittig reaction with a phosphorus ylide compound of the following general formula (7) to form the vinylether compound (1)

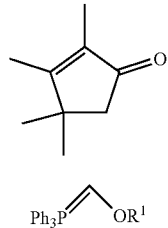 (6)

(7)

wherein, in the general formula (7), R¹ represents a monovalent hydrocarbon group having 1 to 15 carbon atoms, and Ph represents a phenyl group.

9. The process according to claim 4 for preparing the (2,3,4,4-tetramethylcyclopentyl)methyl carboxylate compound (5), the process further comprising subjecting 2,3,4,4-tetramethyl-2-cyclopentenone of the following formula (6) to a Wittig reaction with a phosphorus ylide compound of the following general formula (7) to form the vinylether compound (1)

(6)

(7)

wherein, in the general formula (7), R¹ represents a monovalent hydrocarbon group having 1 to 15 carbon atoms, and Ph represents a phenyl group.

10. A vinylether compound of the following general formula (1):

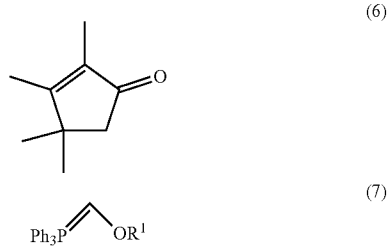 (1)

wherein R¹ represents a monovalent hydrocarbon group having 1 to 15 carbon atoms, and the wavy line represents the E-form, the Z-form, or a mixture thereof.

11. 2,3,4,4-Tetramethyl-1-cyclopentenecarbaldehyde of the following formula (2):

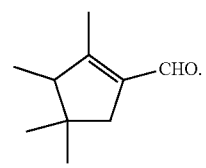 (2)

* * * * *